(12) United States Patent
Anderson

(10) Patent No.: US 7,320,959 B2
(45) Date of Patent: Jan. 22, 2008

(54) USE OF CALMODULIN KINASE II INHIBITORS TO TREAT MYOCARDIAL DYSFUNCTION IN STRUCTURAL HEART DISEASE

(75) Inventor: Mark Anderson, Iowa City, IA (US)

(73) Assignee: Vanderbilt University, Nashville, TN (US)

( * ) Notice: Subject to any disclaimer, the term of this patent is extended or adjusted under 35 U.S.C. 154(b) by 258 days.

(21) Appl. No.: 10/491,323

(22) PCT Filed: Oct. 1, 2002

(86) PCT No.: PCT/US02/31496

§ 371 (c)(1),
(2), (4) Date: Jul. 16, 2004

(87) PCT Pub. No.: WO03/029428

PCT Pub. Date: Apr. 10, 2003

(65) Prior Publication Data

US 2004/0266675 A1    Dec. 30, 2004

Related U.S. Application Data

(60) Provisional application No. 60/328,010, filed on Oct. 8, 2001, provisional application No. 60/326,576, filed on Oct. 1, 2001.

(51) Int. Cl.
*A61K 61/00* (2006.01)
*A01N 25/00* (2006.01)

(52) U.S. Cl. .................... 514/12; 514/789

(58) Field of Classification Search ............ 514/12, 514/789
See application file for complete search history.

(56) References Cited

U.S. PATENT DOCUMENTS

| 3,610,795 A | 10/1971 | Antoine et al. .................. 13/9 |
| 4,897,355 A | 1/1990 | Eppstein et al. ............ 424/450 |
| 6,518,245 B1* | 2/2003 | Anderson et al. ............. 514/14 |

FOREIGN PATENT DOCUMENTS

WO    WO 98/33491    1/1998

OTHER PUBLICATIONS

Tessier et al., Circulation Research, 85(9), 810-819, 1999.*
Anderson al., "KN-93, an Inhibitor of multifunctional Ca++/calmodulin-dependent protein kinase, decreases early afterdepolarizations in rabbit heart." *J Pharm Exp Ther* 1998; 287: 996-1006.
Bagshawe, "The First Bagshawe lecture. Towards generating cytotoxic agents at cancer sites." *Br J Cancer*. Sep. 1989;60(3):275-81. Review.
Bagshawe et al., "A cytotoxic agent can be generated selectively at cancer sites." *Br J Cancer*. Dec. 1988;58(6):700-703.

(Continued)

*Primary Examiner*—Maryam Monshipouri
(74) *Attorney, Agent, or Firm*—Needle & Rosenberg, P.C.

(57) ABSTRACT

The present invention provides a method for treating structural heart disease in a subject, comprising administering an effective amount of an inhibitor of CaMKII to the subject, whereby the administration of the inhibitor treats the structural heart disease in the subject. Also provided are transgenic animal models for treating structural heart disease. Further provided is a means of screening for a compound that can treat structural heart disease.

29 Claims, 17 Drawing Sheets

OTHER PUBLICATIONS

Battelli et al., "T lymphocyte killing by a xanthine-oxidase-containing immunotoxin." *Cancer Immunol Immunother.* 1992;35(6):421-425.

Braun et al., "A Non-Selective Cation Current activated via the multifunctional $Ca^{2+}$-calmodulin-dependent protein kinase in Human Epithelial cells." *J Physiol* 1995; 488: 37-55.

Braun et al., "The multifunctional Calcium/Calmodulin-dependent protein kinase: from form to function." *Ann Rev Physiol* 1995; 57: 417-445.

Brigham et al, "Expression of a prokaryotic gene in cultured lung endothelial cells lipofection with a plasmid vector". *Am J Respir Cell Mol Biol.* Aug. 1989;1(2):95-100.

Brown et al., "Molecular and cellular mechanisms of receptor-mediated endocytosis." *DNA Cell Biol.* Jul.-Aug. 1991;10(6):399-409. Review.

Chang et al. "Characterization of a calmodulin kinase II inhibitor protein in brain." *Proc Natl Acad Sci USA* Sep. 1, 1998;95(18):10890-10895.

Felgner et al., "Lipofection: a highly efficient, lipid-mediated DNA-transfection procedure." *Proc Natl Acad Sci USA* Nov. 1987;(21):7413-7417.

Gottlieb et al., "Effect of beta-blockade on mortality among high-risk and low-risk patients after myocardial infarction." *New England Journal of Medicine* 1998; 339: 489-497.

Hoch et al., "Identification and expression of δ-isoforms of the multifunctional $Ca^{2+}$/Calmodulin-dependent protein kinase in failing and nonfailing human myocardium." *Circulation Research* 1999 ; 84:713-721.

Huang et al., "Transgenic expression of green fluorescence protein can cause dilated cardiomyopathy." *Nat Med* 2000; 6: 482-483.

Hughes et al., "Monoclonal antibody targeting of liposomes to mouse lung in vivo." *Cancer Res.* Nov. 15, 1989;49(22):6214-6220.

Hunt et al., Heart Association. ACC/AHA guidelines for the evaluation and management of chronic heart failure in the adult: executive summary. A report of the American College of Cardiology/American Heart Association Task Force on Practice Guidelines (Committee to revise the 1995 Guidelines for the Evaluation and Management of Heart Failure). *Journal of the American College of Cardiology* 2001; 2101-2113.

Kinugawa al., "Treatment with Dimethylthiourea prevents left ventricular remodeling and failure after experimental myocardial infarction in mice: role of oxidative stress." *Circulation Research* 2000; 87: 392-398.

Litzinger et al., "Biodistribution and immunotargetability of ganglioside-stabilized dioleoylphosphatidylethanolamine liposomes." *Biochem Biophys Acta.* Feb. 17, 1992;1104(1):179-87.

Miyano et al., "Purification and characterization of a brain-specific multifunctional calmodulin-dependent protein kinase from rat cerebellum." *J Biol Chem* 1992;267: 1198-1203.

Molkentin et al., "A calcineurin-dependent transcriptional pathway for cardiac hypertrophy." *Cell* 1998; 93:215-228.

Pfeffer et al., "Angiotensin-converting enzyme inhibition and ventricular remodeling after myocardial infarction." *Ann Rev Physiol* 1995; 57:805-826.

Pietersz et al., "Antibody conjugates for the treatment of cancer." *Immunol Rev.* Oct. 1992;129:58-80. Review.

Pitt et al., "The effect of spironolactone on morbidity and mortality in patients with severe heart failure. Randomized Aldactone Evaluation Study Investigators." *New England Journal of Medicine* 1999; 341: 709-717.

Rhoads A., Friedberg F. "Sequence motifs for calmodulin recognition." *FASEB J.* 1997; 11: 331-340.

Roffler et al., "Anti-neoplastic glucuronide prodrug treatment of human tumor cells targeted with a monoclonal antibody-enzyme conjugate." *Biochem Pharmacol.* Oct. 24, 1991;42(10):2062-2065.

Sam et al., "Progressive left ventricular remodeling and apoptosis late after myocardial infarction in mouse heart." *American Journal of Physiology-Heart & Circulatory Physiology* 2000; 279: H422-H428.

Senter et al., "Generation of cytotoxic agents by targeted enzymes." *Bioconjug Chem.* Jan.-Feb. 1993;4(1):3-9. Review.

Senter et al., "Generation of 5-fluorouracil from 5-fluorocytosine by monoclonal antibody-cytosine deaminase conjugates." *Bioconjug Chem.*, Nov.-Dec. 1991;2(6):447-451.

Spencer et al., "Twenty year trends (1975-1995) in the incidence, in-hospital and long-term death rates associated with heart failure complicating acute myocardial infarction: a community-wide perspective." *J Am Coll Cardiol* 1999; 34:1378-1387.

Sussman et al., "Prevention of cardiac hypertrophy in mice by calcineurin inhibition." *Science* 1998; 281: 1690-1693.

Tokumitsu et al., "Activation mechanisms for $Ca^{2+}$/Calmodulin-dependent protein kinase IV. Identification of a brain CaM-kinase IV kinase." *J Biol Chem* 1994; 269:28640-28647.

Trueblood et al., "Exaggerated left ventricular dilation and reduced collagen deposition after myocardial infarction in mice lacking osteopontin." *Circulation Research* 2001; 88:1080-1087.

Vaughn et al., "Post-myocardial infarction ventricular remodeling: animal and human studies." *Cardiovascular Drugs & Therapy* 1994; 8: 453-460.

Wu et al., "CaM kinase augments cardiac L-type $Ca^{2+}$current: a cellular mechanism for long Q-T arrhythmias." *American Journal of Physiology* 1999; 276:H2168-H2178.

Wu et al., "Calmodulin kinase II and arrhythmias in a mouse model of cardiac hypertrophy." *Circ.* 2002;106:1288-1293.

* cited by examiner

USE OF CALMODULIN KINASE II INHIBITORS TO TREAT MYOCARDIAL DYSFUNCTION IN STRUCTURAL HEART DISEASE

This application claims the benefit of U.S. Provisional Application No. 60/326,576, filed Oct. 1, 2001 and U.S. Provisional Application No. 60/328,010, filed Oct. 8, 2001. The aforementioned applications are hereby incorporated herein by reference in their entirety.

This invention was made with government support under HL03727 and HL62494 awarded by the National Institutes of Health. The government has certain rights in the invention.

BACKGROUND

1. Field of the Invention

The invention relates to the inhibition of Calmodulin kinase II (CaMKII). More specifically, the CaMKII inhibition can treat or prevent structural heart disease, for example contractile dysfunction following a myocardial infarction, or dilated cardiomyopathy.

2. Background Art

Myocardial infarction is a major cause of significant disability and death in the United States and in many other countries around the world, and accounts for approximately ⅔ of all heart failure.[7]

Several disease-initiating events (e.g. myocardial infarction, untreated hypertension, congenital mutations of contractile proteins) can result in a common heart disease phenotype that consists of dilation of the cardiac chambers, resulting in reduction in contractile function (i.e., a decrease in the fraction of total blood ejected from each chamber during systole) that leads to the clinical syndrome of heart failure. Dilated cardiomyopathy includes two distinct disease entities. Dilated cardiomyopathy, as used herein, includes ischemic cardiomyopathy which is a disease entity characterized by left ventricular dilation and reduced contractile function. This condition can result after myocardial infarction when the normal compensatory hypertrophy of surviving, non-infarcted myocardium is insufficient.[7] "Dilated cardiomyopathy" can also include increased myocardial mass and reduced contractile function due to a genetic abnormality of myocardial proteins in the absence of myocardial infarction.[7] A subject with dilated cardiomyopathy is a subject who has decreased cardiac contractility due to dilation of the ventricles. Thus, a subject with dilated cardiomyopathy and contractile dysfunction has different and more severe dysfunction than a subject in whom hypertrophy of surviving non-infarcted myocardium has compensated for infarcted myocardium. Further, a subject with dilated cardiomyopathy and contractile dysfunction has disease that is distinct from other cardiac conditions including abnormal relaxation (i.e., diastolic dysfunction and cardiac arrhythmia.

Available therapies for heart failure are insufficient, and new methods of treatment are needed. The heart responds to infarction by hypertrophy of surviving cardiac muscle in an attempt to maintain normal contraction. However, when the hypertrophy is insufficient to compensate, dilated cardiomyopathy and reduced contractile function result, leading to heart failure and death.[19] Despite important advances in medical therapies for preventing cardiac dysfunction and heart failure after myocardial infarction,[15] these problems remain a significant unsolved public health problem.

No pharmacological therapy for dilated cardiomyopathy is curative or satisfactory, and many patients die or, in selected cases, undergo heart transplantation. Presently available pharmacological therapies for reducing cardiac dysfunction and reducing mortality in patients with heart failure fall into three main categories: angiotensin-converting enzyme (ACE) inhibitors, beta adrenergic receptor (βAR) antagonists, and aldosterone antagonists. Despite reducing mortality, patients treated with these medicines remain at significantly increased risk for death compared to age-matched control patients without heart failure. ACE inhibitors,[11] βAR antagonists[4] and (at least one type of) aldosterone receptor antagonist[12] can significantly reduce the incidence and extent of cardiac dysfunction and heart failure after myocardial infarction. Other available pharmacological therapies include nitroglycerin, diuretics, positive inotropic agents (cardiac stimulants), and brain natriuretic peptide (BNP). These latter agents can provide symptomatic relief, but are not associated with reduced mortality in heart failure patients.

ACE inhibitors are associated with cough in 10% of patients and can result in renal failure in the setting of bilateral renal artery stenosis or other severe kidney disease.[7] βAR antagonists are associated with impotence and depression, and are contraindicated in patients with asthma; furthermore, patients may develop worsened heart failure, hypotension, bradycardia, heart block, and fatigue with initiation of βAR antagonists[7] Aldosterone receptor antagonism causes significant hyperkalemia and painful gynecomastia in 10% of male patients.[7,12] Agents without a demonstrated mortality benefit are also associated with problems; most notable is the consistent finding that many cardiac stimulants improve symptoms, but actually increase mortality,[7] likely by triggering lethal cardiac arrhythmias. In contrast, CaMKII inhibition is now known to reduce cardiac arrhythmias in animal models,[20,21] and so represents a novel approach to enhancing cardiac function without increasing arrhythmias. Presently available pharmacological therapies are ineffective and are limited by significant unwanted side effects, and so development of new therapies with improved efficacy and less severe side effects is an important public health goal.

Calmodulin kinase II is an enzyme that is present in heart and is activated when $Ca^{2+}$ increases inside the heart cells, and binds to the $Ca^{2+}$ binding protein calmodulin.[3] CaMKII activity can increase in patients with severe cardiomyopathy, but CaMKII has never been linked to dilated cardiomyopathy or deterioration of contraction in heart failure.

The present invention provides methods of improving (increasing) contractile function of the myocardium to treat dilated cardiomyopathy and heart failure by inhibiting CaMKII. The present invention further provides mouse models of cardiac-targeted CaMKII inhibition by transgenic over expression of a selective CaMKII inhibitory peptide, AC3-I. Thus, the present AC3-I transgenic mouse is an important new tool to test for the effects of chronic CaMKII inhibition in cardiac disease.

SUMMARY OF THE INVENTION

The present invention provides a method of treating or preventing myocardial dysfunction that follows myocardial infarction in a subject, comprising administering to the subject an effective amount of an inhibitor of Calmodulin Kinase II (CaMKII), whereby the administration of the inhibitor improves myocardial contraction after a myocardial infarction in the subject.

The present invention provides a method of treating or preventing myocardial dysfunction that occurs in dilated cardiomyopathy or other structural heart disease (e.g., end-stage valve disease) in a subject diagnosed with dilated cardiomyopathy or other structural heart disease, comprising administering to the subject an effective amount of an inhibitor of CaMKII, whereby the administration of the inhibitor treats or prevents dilated cardiomyopathy or other structural heart disease in the subject.

The present invention provides a method of treating or preventing myocardial dysfunction that occurs in dilated cardiomyopathy in a subject diagnosed with dilated cardiomyopathy, comprising administering to the subject an effective amount of an inhibitor of CaMKII, whereby the administration of the inhibitor treats or prevents dilated cardiomyopathy or other structural heart disease in the subject.

The present invention provides a method of increasing myocardial contractility in a subject diagnosed with dilated cardiomyopathy, comprising administering to the subject an effective amount of an inhibitor of CaMKII, whereby the administration of the inhibitor increases myocardial contractility in the subject.

Further provided by the present invention is a method of increasing myocardial contractility in a subject diagnosed with cardiac dysfunction and/or decreased contractility following a myocardial infarction, comprising administering to the subject an effective amount of an inhibitor of CaMKII, whereby the administration of the inhibitor increases myocardial contractility in the subject.

Further provided by the present invention is a method of increasing myocardial contractility in a subject diagnosed with decreased myocardial contractility following a myocardial infarction, comprising administering to the subject an effective amount of an inhibitor of CaMKII, whereby the administration of the inhibitor increases myocardial contractility in the subject.

The present invention provides a method of identifying a compound that can treat structural heart disease, comprising: a) measuring cardiac contractility in an animal with structural heart disease; b) administering the compound to the animal of step (a); c) measuring cardiac contractility in the animal of step (b); and detecting an increase in cardiac contractility in the animal of step (b) compared to cardiac contractility in the animal of step (a), whereby the detection of an increase in cardiac contractility identifies a compound that can treat structural heart disease.

The present invention provides a method of treating structural heart disease in a subject, comprising administering to the subject an effective amount of a compound identified by the method of the present invention.

The present invention provides a transgenic animal, which expresses a nucleic acid encoding an inhibitor of CaMKII.

The present invention also provides a transgenic animal which expresses a nucleic acid encoding a peptide comprising the peptide of SEQ ID NO:8, which is referred to as AC3-C.

The present invention further provides a dual transgenic animal, which expresses a nucleic acid encoding an inhibitor of CaMKII and a nucleic acid expressing calcineurin.

DETAILED DESCRIPTION OF THE INVENTION

Figure 1:
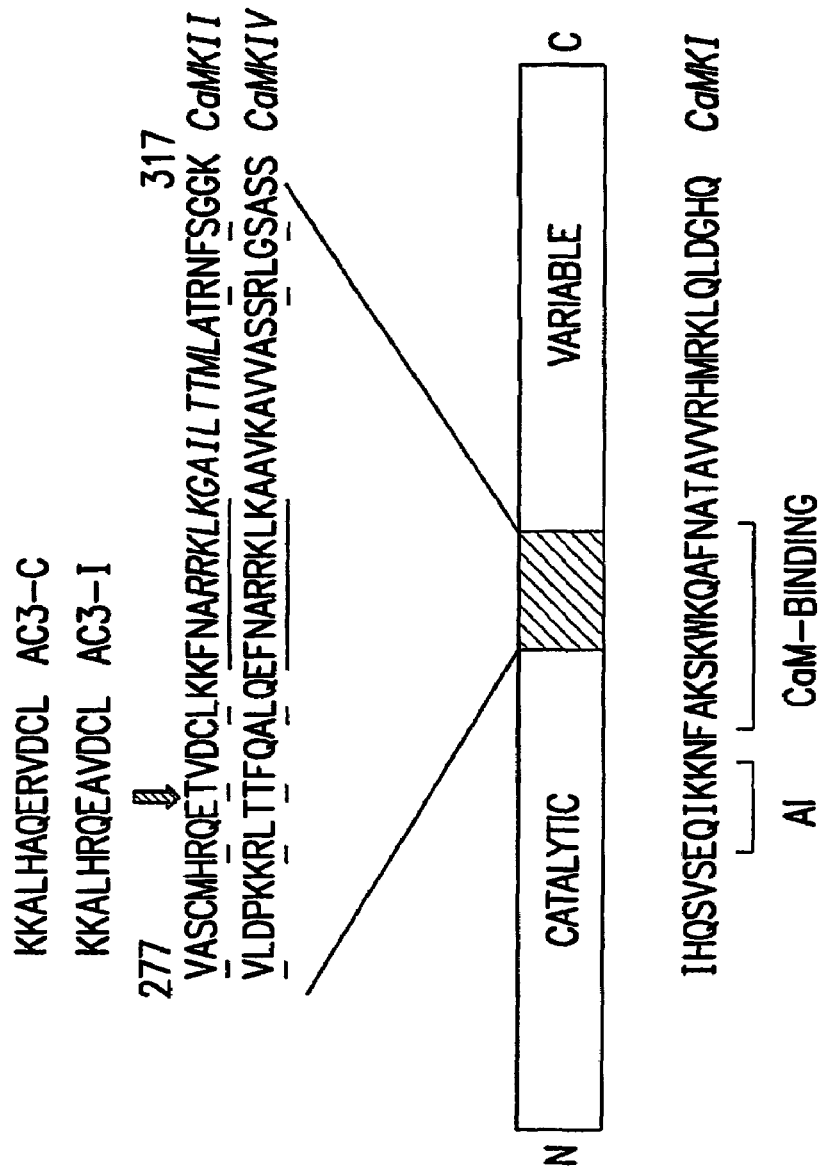
FIG. 1. A diagram of the domain structures of CaMK I, II, and IV, and the CaMKII inhibitory and control peptides expressed in the AC3-I and AC3-C transgenic mice engineered for the present studies. CaMKII and IV both have a regulatory domain (black rectangle) that consists of CaM-binding and autoinhibitory (AI) regions. The CaM binding region of CaMKII (296-309, numbered according to CaMKII and marked by italics) is very similar in CaMKIV (identical amino acids are underlined), and inhibitory peptides directed against the CaM-binding sequence in CaMKII similarly inhibit activation of CaMKIV[17]. AC3-I is modeled on the AI region of CaMKII that is centered around Thr 286 (marked with an arrow), and is dissimilar in CaMKII and CaMKIV. Neither the CaM-binding or AI regions of CaMKI are homologous to CaMKII or IV, but, in contrast to the AI region, inhibitory peptides directed against the CaM-binding region of CaMKII or IV may nevertheless inhibit CaMKI because CaM-binding domains commonly share an a helical structure, but often lack primary sequence homology.[13]
Figure 2A:
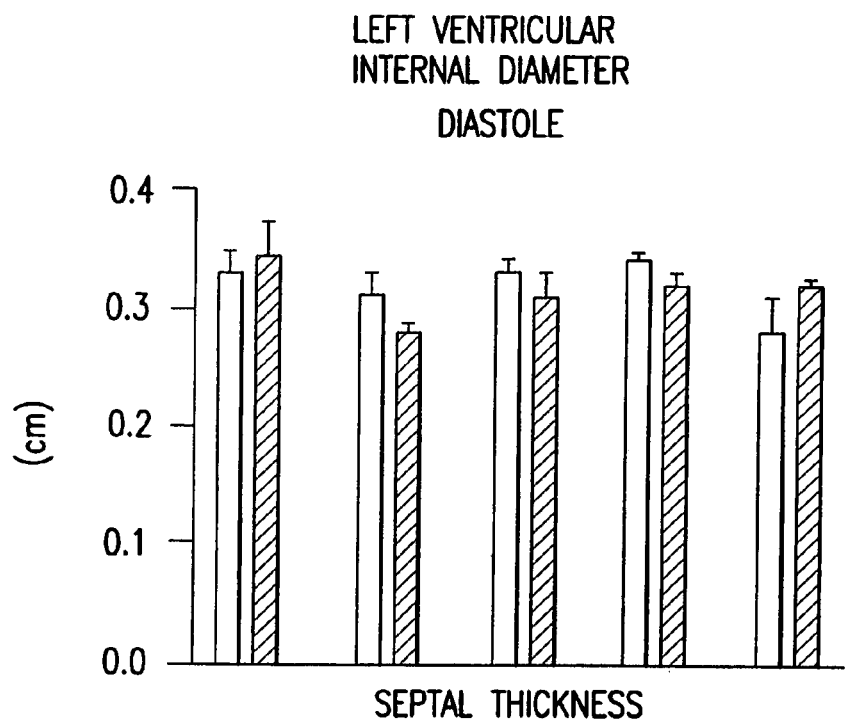
FIGS. 2A-E. AC3-I mice have normal cardiac size and systolic function. A and B. Echocardiographic left ventricular dimensions are not significantly different between AC3-I mice and wild-type (WT) littermate controls in diastole (A) or systole (B). C and D. Interventricular septal thickness is not different between AC3-I mice and WT littermate controls in diastole (C) or systole (D). E. Left ventricular fractional shortening is not different between AC3-I and WT littermate control mice at baseline. Open bars are WT and black bars are AC3-I transgenic (TG) in all panels. The number of mice studied (n) in each line number (indicated in panel E) is the same in all panels.
Figure 2B:
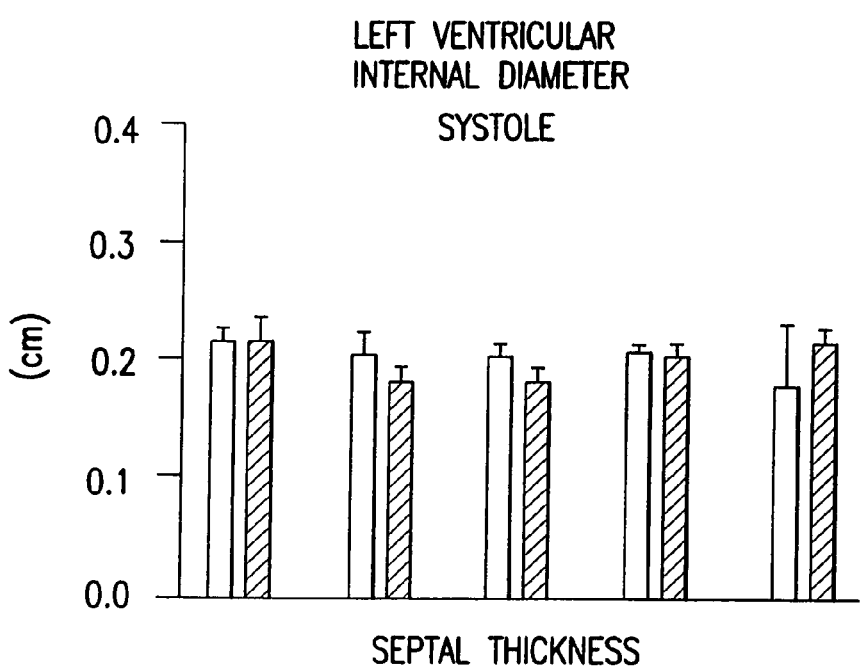
Figure 2C:
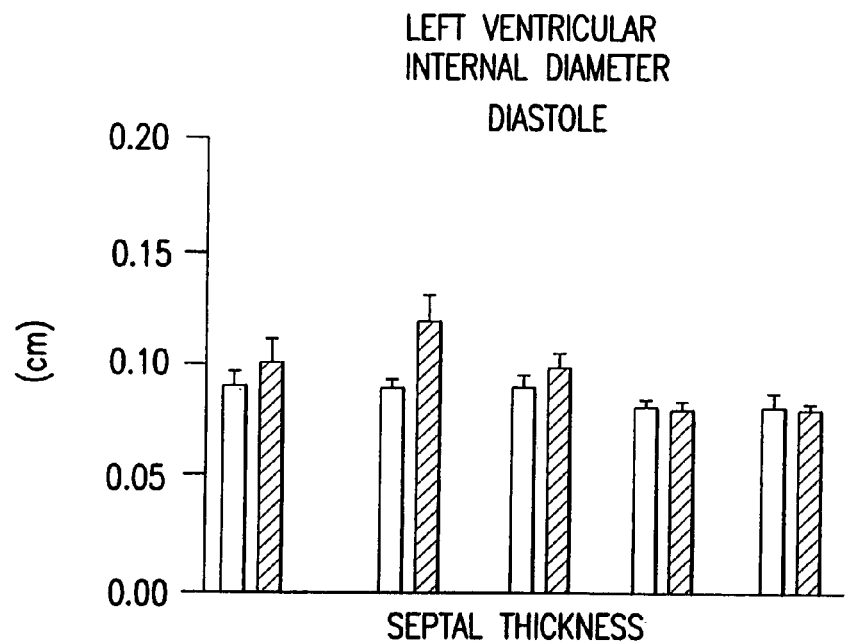
Figure 2D:
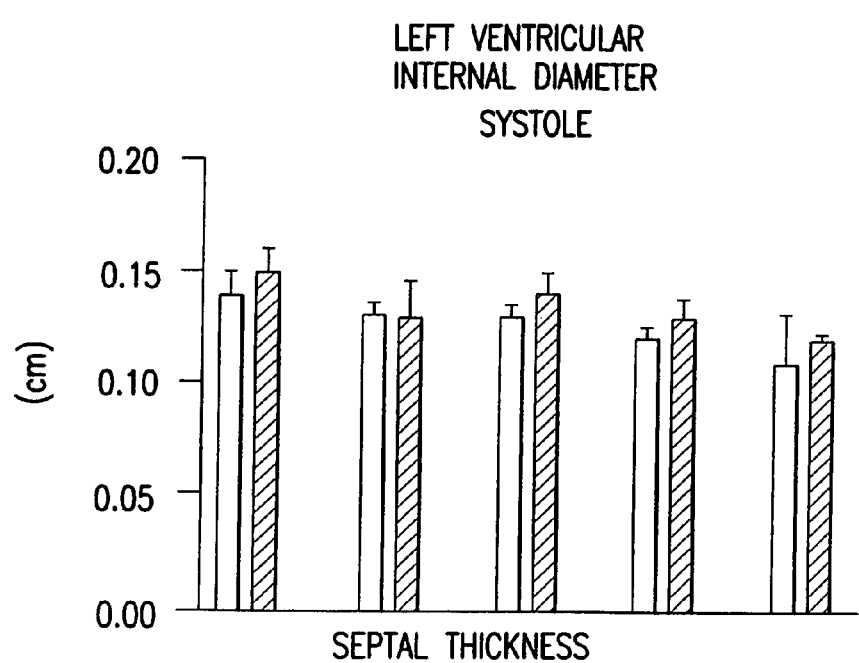
Figure 2E:
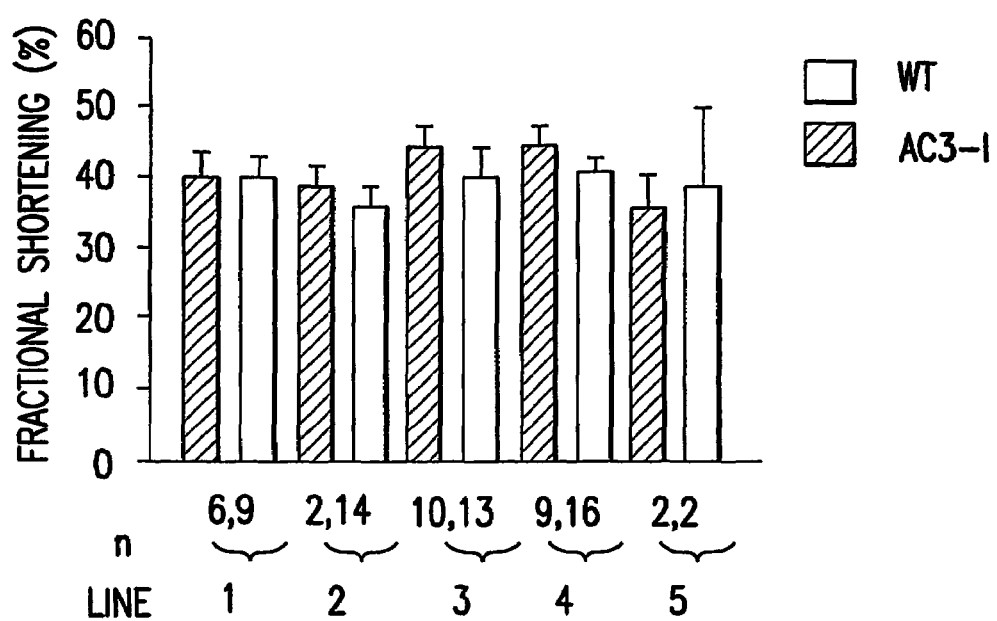

It must be noted that, as used in the specification and the appended claims, the singular forms "a," "an," and "the" include plural referents unless the context clearly dictates otherwise. Thus, for example, reference to "an inhibitor" includes multiple copies of the inhibitor and can also include more than one particular species of inhibitor.

The present invention provides a method of treating or preventing myocardial contractile dysfunction after a myocardial infarction in a subject diagnosed with myocardial contractile dysfunction after a myocardial infarction, comprising administering to the subject an effective amount of an inhibitor of Calmodulin Kinase II (CaMKII), whereby the administration of the inhibitor treats or prevents myocardial contractile dysfunction after myocardial infarction in the subject In general, an "effective amount" of an inhibitor is that amount needed to achieve the desired result or results. By "myocardial infarction" is meant an ischemic injury to the heart in which part of the myocardium (heart muscle) has undergone necrosis or apoptosis, i.e., programmed cell death. An "ischemic injury" means the damage or potential damage to an organ or tissue that results from the interruption of blood flow to the organ or tissue, i.e., an ischemic event. As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human.

The subject can be a patient diagnosed as having a myocardial infarction. The subject can be a patient diagnosed as having post-infarction cardiac dysfunction. The subject can be a patient who has been diagnosed as having had a myocardial infarction who is, thus, at increased risk of developing post-infarction cardiac dysfunction. Further, the subject can be a patient diagnosed as having dilated cardiomyopathy or symptoms of heart failure from any cause associated with a phenotype of cardiac chamber dilation and reduced myocardial contractile function. The subject can be a patient diagnosed as having reduced myocardial contractility. Methods of diagnosing myocardial infarction, post-infarction cardiac dysfunction, reduced myocardial contractility and dilated cardiomyopathy are well known in the art. Methods of distinguishing subjects having post-infarction contractile dysfunction or dilated cardiomyopathy from subjects having myocardial infarction or having myocardial hypertrophy are well known in the art. It is recognized that a subject diagnosed with myocardial infarction, or a subject diagnosed with cardiac arrhythmia, or a subject diagnosed with myocardial hypertrophy does not necessarily have dilated cardiomyopathy or reduced myocardial contractility.

An inhibitor of CaMKII can be any compound, composition or agent that inhibits the activity or expression (e.g., the amount or the disease-causing effect) of CaMKII. The compound can be a peptide or non-peptide agent, including, for example, a nucleic acid that encodes a peptide inhibitor. Moreover, the agent can be an antisense nucleic acid that inhibits expression of CaMKII in the heart (see GenBank accession numbers L13407 for isoform δ3 and δ2 from Hoch et al., Circ Res 1999 in FIG. 9 of this application)[5] By "inhibit" is meant to restrict, hold back or reduce. Thus, an inhibitor is an agent that can, for example, reduce an activity of an enzyme or the amount of expression of an enzyme, or both. The inhibition can be reversible or irreversible. CaMKII activity in a subject or the amount of CaMKII in a subject can be readily determined based on detection or measurement of a functional response, for example as determined by echocardiography or by other clinical parameters. Specific methods of measuring CaMKII activity in a non-human animal model are provided herein. Thus, it is routine to identify compounds that inhibit CaMKII.

An example of an inhibitor of CaMKII is a peptide comprising the peptide of SEQ ID NO:2, which is also referred to herein as AC3-I. The inhibitor of the invention can consist of the peptide of SEQ ID NO:2.

Another example of an inhibitor of CaMKII is a peptide comprising the peptide of SEQ ID NO:4, which is CaM-KIIN. The inhibitor can be the full-length CaM-KIIN (SEQ ID NO:4) and/or a fragment of the full-length peptide; the fragment is called CaM-KIINtide (SEQ ID NO:6). CaMKIIN and CaM-KIINtide are described in Chang et al. PNAS (USA) 1998 95:10890-10895, which is herein incorporated by reference in its entirety.

Because each of these is shown to inhibit CaMKII, it is expected that other peptides and polypeptides that contain it but include non-essential amino acids will have similar activity. A non-essential amino acid is an amino acid that will not affect the function of the peptide or the way the peptide accomplishes that function (e.g., its secondary structure or the ultimate result of the activity of the peptide). Examples of non-essential amino acids in the present invention include, but are not limited to, the amino acids comprising GFP, a peptide label that tags and identifies proteins or peptides for purification There are numerous other inhibitors of CaMKII that are contemplated by the present invention, one of which is KN-93. KN-93, a non-peptide inhibitor of CaMKII, is described in WO 98/33491, which is herein incorporated by reference in its entirety for its teaching with regard to KN-93 and inhibitors of CaMKII.

The present invention further provides a method of treating or preventing cardiac dysfunction following myocardial infarction in a subject, comprising administering to the subject an effective amount of an inhibitor of CaMKII, whereby the administration of the inhibitor treats or prevents the cardiac dysfunction in the subject. By "cardiac dysfunction" is meant reduced contractile function of the blood pumping chambers that results in the clinical condition of heart failure. Methods of diagnosing cardiac dysfunction following a myocardial infarction in a subject are well known in the art.

In the method of treating or preventing cardiac dysfunction following a myocardial infarction in a subject, the inhibitor of CaMKII can be a peptide, for example, a peptide comprising the peptide of SEQ ID NO:2, or a peptide consisting of the peptide of SEQ ID NO:2. The inhibitor of CaMKII can be a peptide comprising the peptide of SEQ ID NO:4 or a peptide consisting of the peptide of SEQ ID NO:4. Further, the inhibitor can be a peptide comprising the peptide SEQ ID NO:6 or a peptide consisting of the peptide of SEQ ID NO:6. The inhibitor can be a non-peptide inhibitor, for example, an inhibitor comprising the active region of KN-93 or it can be KN-93.

The present invention also provides a method of treating or preventing dilated cardiomyopathy or any heart disease with the phenotypes of cardiac chamber dilation from any cause in a subject, comprising administering to the subject an effective amount of an inhibitor of CaMKII, whereby the administration of the inhibitor treats dilated cardiomyopathy or reduces cardiac chamber dilation in the subject. Methods of diagnosing dilated cardiomyopathy in a subject are well known in the art.

In the method of treating or preventing dilated cardiomyopathy, the inhibitor of CaMKII can be a peptide, for example, a peptide comprising the peptide of SEQ ID NO:2, or a peptide consisting of the peptide of SEQ ID NO:2. The inhibitor of CaMKII can be a peptide comprising the peptide of SEQ ID NO:4 or a peptide consisting of the peptide of SEQ ID NO:4. Further, the inhibitor can be a peptide comprising the peptide SEQ ID NO:6 or a peptide consisting of the peptide of SEQ ID NO:6. The inhibitor can be a non-peptide inhibitor, for example, an inhibitor comprising the active region of KN-93 or it can be KN-93.

The present invention provides a method of increasing myocardial contractility in a subject diagnosed with dilated cardiomyopathy or any heart disease with the phenotypes of cardiac chamber dilation or reduced contractile function from any cause, comprising administering to the subject an effective amount of an inhibitor of CaMKII, whereby the administration of the inhibitor improves myocardial contractility in the subject. Techniques for measuring cardiac contractility, for example echocardiography, radionucleotide angiography, and magnetic resonance imaging are well known in the art. As used herein, "myocardial contractility" is a measure of the contraction of the heart muscle, more specifically, of the left ventricle. As shown in FIG. 7, AC3-I and KN-93 increase myocardial contractility (a positive inotropic effect) without affecting cardiac hypertrophy.

Further, the present invention provides a method of increasing myocardial contractility in a subject diagnosed with myocardial infarction, comprising administering to the subject an effective amount of an inhibitor of CaMKI, whereby the administration of the inhibitor improves myocardial contractility in the subject.

The present invention also provides a method of increasing myocardial contractility in a subject diagnosed with cardiac dysfunction following a myocardial infarction, comprising administering to the subject an effective amount of an inhibitor of CaMKII, whereby the administration of the inhibitor improves myocardial contractility in the subject.

In the method of increasing myocardial contractility, the inhibitor of CaMKII can be a peptide, for example, a peptide comprising the peptide of SEQ ID NO:2, or a peptide consisting of the peptide of SEQ ID NO:2. The inhibitor of CaMKII can be a peptide comprising the peptide of SEQ ID NO:4 or a peptide consisting of the peptide of SEQ ID NO:4. Further, the inhibitor can be a peptide comprising the peptide SEQ ID NO:6 or a peptide consisting of the peptide of SEQ ID NO:6. The inhibitor can be a non-peptide inhibitor, for example, an inhibitor comprising the active region of KN-93 or it can be KN-93.

An inhibitor of CaMKII can be used to increase contractility of the myocardium without affecting myocardial hypertrophy, thereby treating a subject diagnosed with myocardial infarction, cardiac dysfunction following a myocardial infarction and/or dilated cardiomyopathy.

The present invention provides a method of identifying a compound that can treat structural heart disease, comprising: a) measuring cardiac contractility in an animal with structural heart disease; b) administering the compound to the animal of step (a); c) measuring cardiac contractility in the animal of step (b); and d) detecting an increase in cardiac contractility in the animal of step (b) compared to cardiac contractility in the animal of step (a), whereby the detection of an increase in cardiac contractility identifies a compound that can treat structural heart disease. In the method of this invention, the animal with structural heart disease can be a transgenic animal that expresses AC3-C. Methods of measuring cardiac contractility are well known in the art and include, but are not limited to, echocardiography. Such methods include radionucleotide angiography, magnetic resonance imaging, and left ventricular angiography.

The present invention provides a method of identifying a compound that can treat structural heart disease, comprising: a) measuring brain natriuretic peptide in an animal with structural heart disease; b) administering the compound to the animal of step (a); c) measuring brain natriuretic peptide in the animal of step (b); and d) detecting an increase in brain natriuretic peptide in the animal of step (b) compared to brain natriuretic peptide in the animal of step (a), whereby the detection of an increase in brain natriuretic peptide identifies a compound that can treat structural heart disease. In the method of this invention, the animal with structural heart disease can be a transgenic animal that expresses AC3-C.

Heart failure is a clinical syndrome that includes reduced exercise tolerance due to reduction in cardiac contraction and tissue oxygenation,7 so exercise testing by treadmill or bicycle ergonometry, reduced tissue oxygen uptake, or increased plasma brain natriuretic peptide levels are all markers of heart failure severity. Values denoting extreme and moderate impairment of myocardial contraction, exercise capacity, maximum oxygen consumption, and circulating brain natriuretic peptide levels are well described and known to one skilled in the art of treating heart failure.[7] Examples of structural heart disease include, but are not limited to, myocardial infarction, cardiac dysfunction following myocardial infarction, reduced myocardial contractility and dilated cardiomyopathy.

The present invention provides a method of treating myocardial infarction, cardiac dysfunction following myocardial infarction and/or dilated cardiomyopathy in a subject, comprising administering to the subject an effective amount of the compound identified by the above-described method, whereby the administration of the compound to the subject treats cardiac dysfunction following myocardial infarction and/or dilated cardiomyopathy or patients with heart failure and dilated cardiac chambers and reduced left ventricular contractility.

The present invention provides a transgenic animal that expresses a nucleic acid encoding an inhibitor of CaMKII. By "transgenic animal" is meant an animal in which all the cells of its body comprise an exogenous nucleic acid. In one example of a transgenic animal of the invention, the transgene is specifically expressed in heart muscle cells, driven by a heart cell specific promoter. This mouse was engineered with a cardiac-specific α myosin heavy chain promoter (GenBank accession U71441). Methods of making transgenic animals are well known in the art, and specifically exemplified herein.

In the transgenic animal of the present invention, the inhibitor of CaMKII that is expressed can be a peptide comprising the peptide of SEQ ID NO:2. Moreover, the transgenic animal of the invention can express the peptide consisting of the peptide of SEQ ID NO:2. Recent reports have found at least 4 varieties of the CaMKII δ isoform in heart,[5] and AC3-I (SEQ ID NO:2) inhibits all CaMKII isoforms, due to conservation of the targeted regulatory domain. The AC3-I targeted domain in CaMKII is dissimilar to analogous functional domains in other CaMK types (i.e. CaMKI and CaMKIV, FIG. 1), and is virtually devoid of activity against protein kinases A and C.[3]

In the transgenic animal of the invention, the inhibitor of CaMKII that is expressed can be a peptide comprising the peptide of SEQ ID NO:4. Moreover, the transgenic animal of the invention can express the peptide consisting of the peptide of SEQ ID NO:4.

Figure 4:
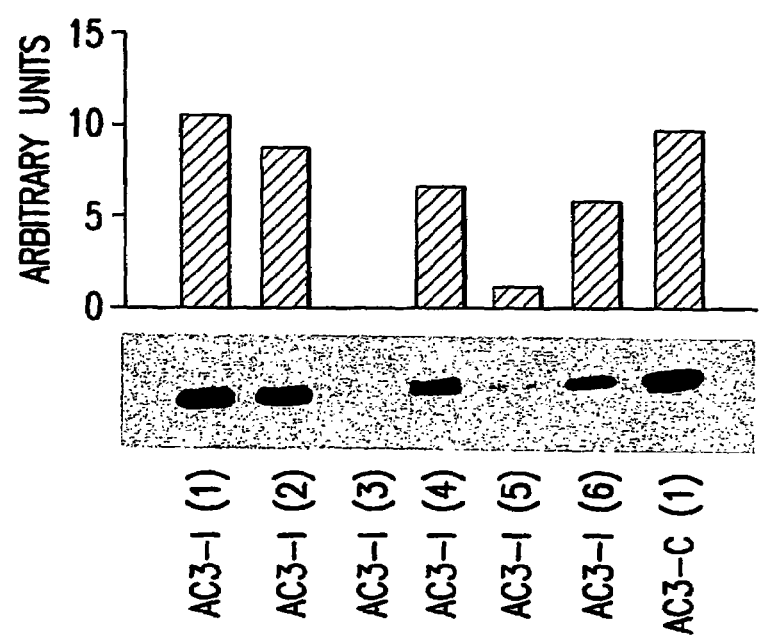
FIG. 4. Transgene expression in AC3-I and AC3-C mice by GFP Western blots. Line numbers are indicated in parenthesis to indicate identity in Western blots and corresponding quantitative phosphorimaging (data normalized to AC3-I line 5). The genetic identity of all transgenic mice was confirmed by Southern analysis, but AC3-I line 3 did not express the transgene.
Figure 5A:
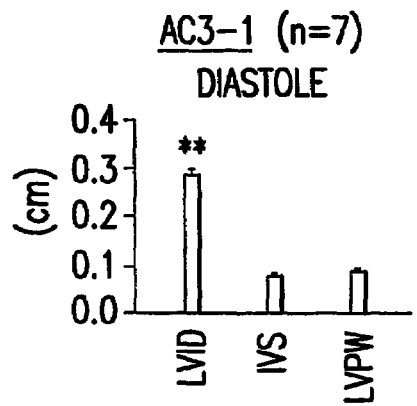
FIGS. 5A-D. AC3-C transgenic mice (from line 1) develop dilated cardiomyopathy. The left ventricular internal diameter (LVID) is significantly greater in AC3-C (B) than AC3-I mice (B, P<0.01, from line 4) in diastole, indicating a dilated phenotype. The LVID shortens significantly less in AC3-C (B) than in AC3-I (A, *P<0.001) mice during systole, indicating reduced ventricular function. In contrast to LVID, the interventricular septum (IVS) and the left ventricular posterior wall (LVPW) are not significantly different between AC3-I and AC3-C mice in diastole or systole. C. Left ventricular fractional shortening is significantly depressed in AC3-C compared to AC3-I mice (P<0.001). D. The heart rates are not different between AC3-I and AC3-C mice.
Figure 5A:
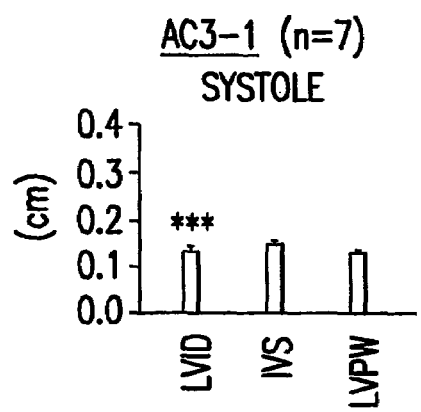
Figure 5B:
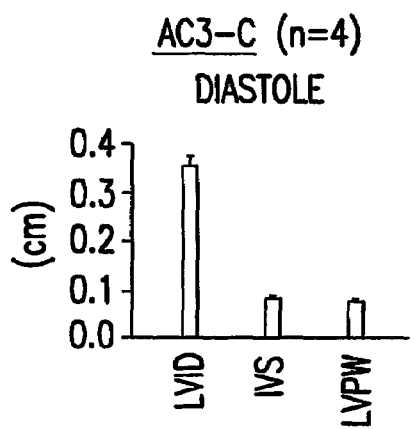
Figure 5B:
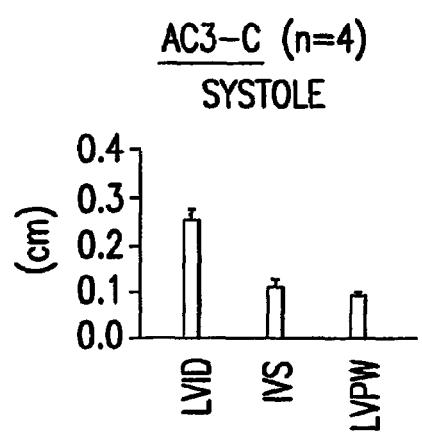
Figure 5C:
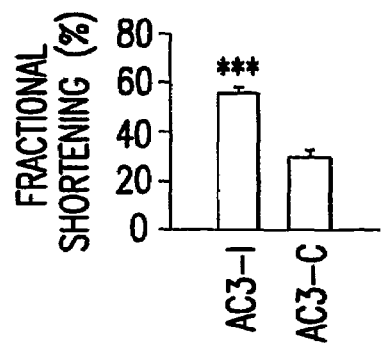
Figure 5D:
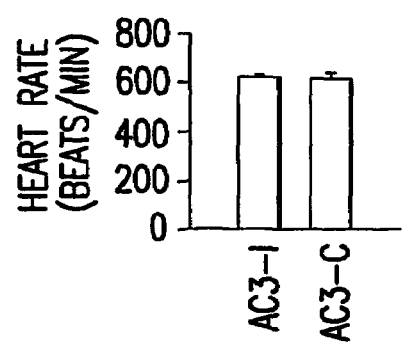
Figure 6A:
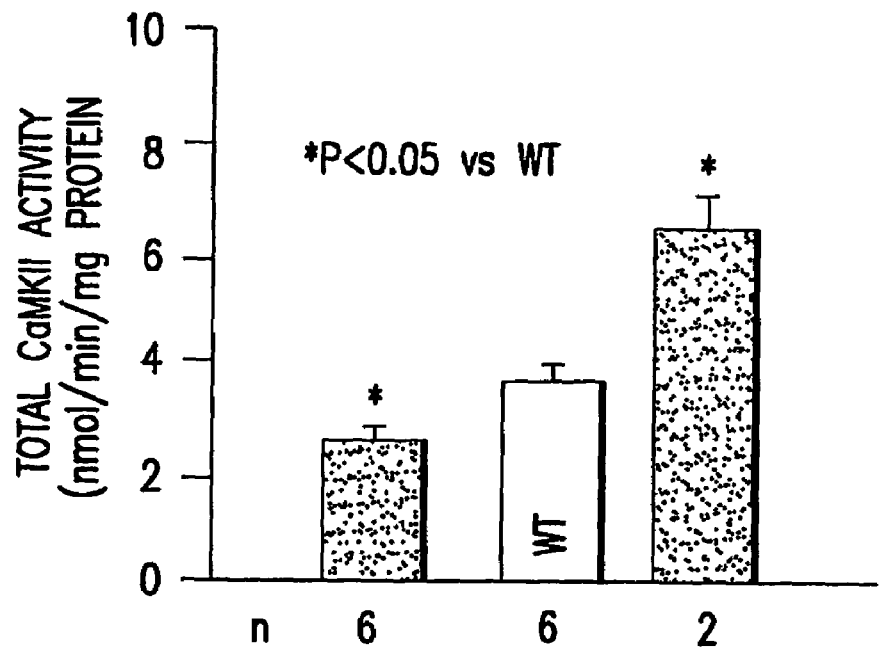
FIGS. 6A-B. Total CaMKII activity is significantly reduced in ventricular homogenates from AC3-I compared to AC3-C mice and wild-type (WT) littermates. A. Total CaMKII activity. B. $Ca^{2+}$-independent fraction of CaMKII activity.
Figure 6B:
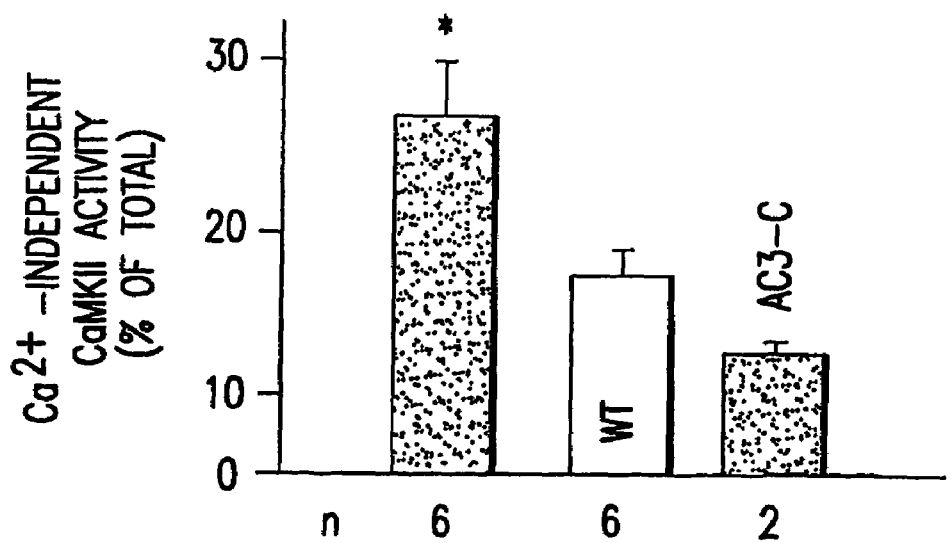
Figure 7A:
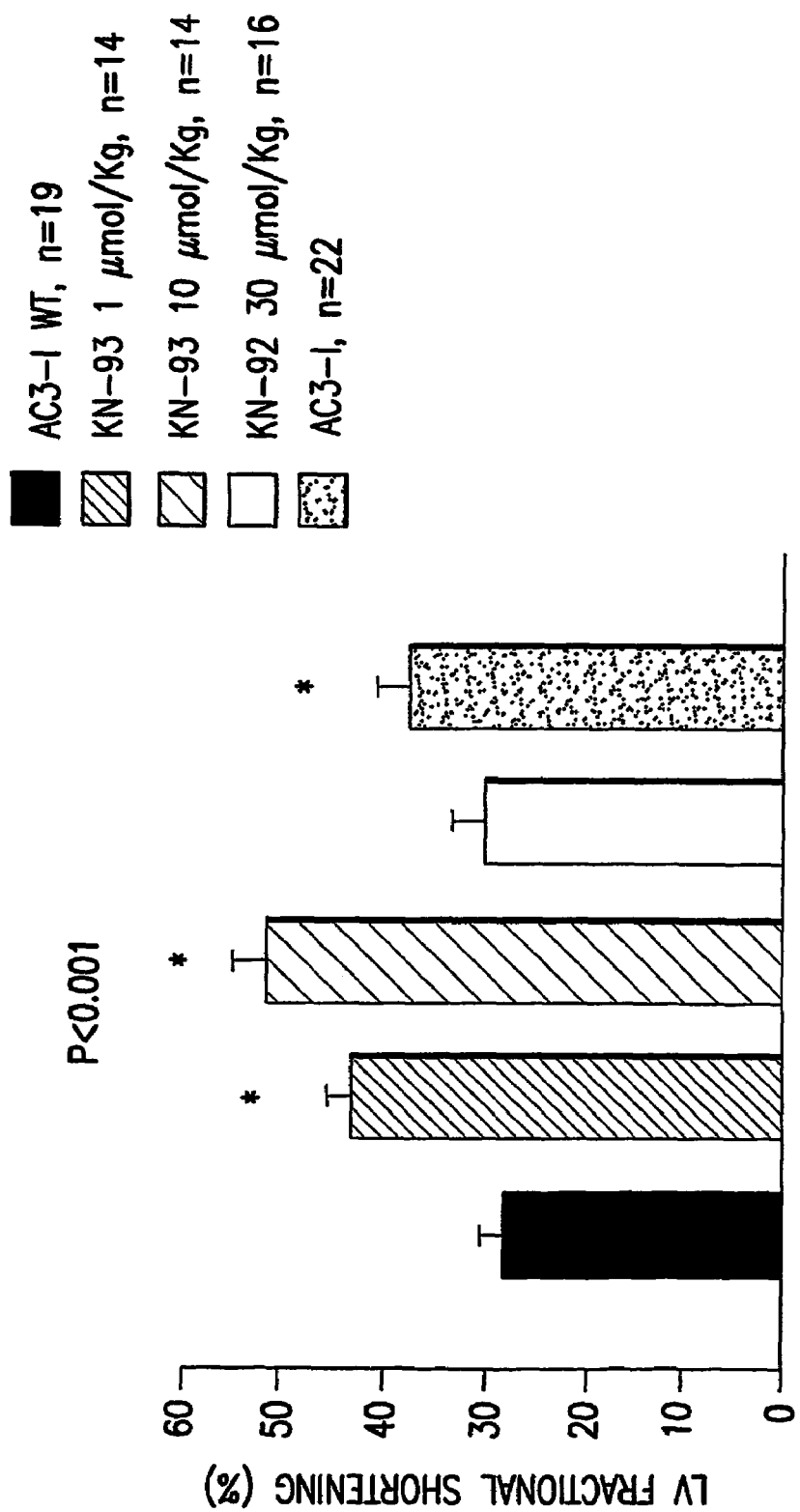
FIGS. 7A-D. CaMKII inhibition improves contractile function after myocardial infarction surgery. Echocardiographic measurements in unanesthetized mice 3 weeks after myocardial infarction surgery reveal significantly preserved left ventricular function in mice with CaMKII inhibition. A. Left ventricular (LV) fractional shortening is significantly greater in mice treated daily with the CaMKII inhibitory agent KN-93 (at 1 and 10 μmol/Kg body weight) and in AC3-I mice with transgenically targeted CaMKII inhibition than in wild type littermate controls (WT) or in WT mice treated daily with the inactive KN-93 congener KN-92 (30 μmol/Kg body weight). P<0.001 by ANOVA and asterisks indicate a significant difference compared to WT using a Bonferroni corrected t test. B. LV internal diameter (LVID) during diastole is a marker of LV chamber dilation. No significant differences in LVID during diastole were present between groups. C. LV posterior wall (LVPW) wall thickness in diastole is a measure of LV hypertrophy of the non-infarcted wall. No significant differences in LVPW in diastole were present between groups. D. Heart rate was significantly slower in AC3-I mice with transgenically targeted CaMKII inhibition compared to all other groups.
Figure 7B:
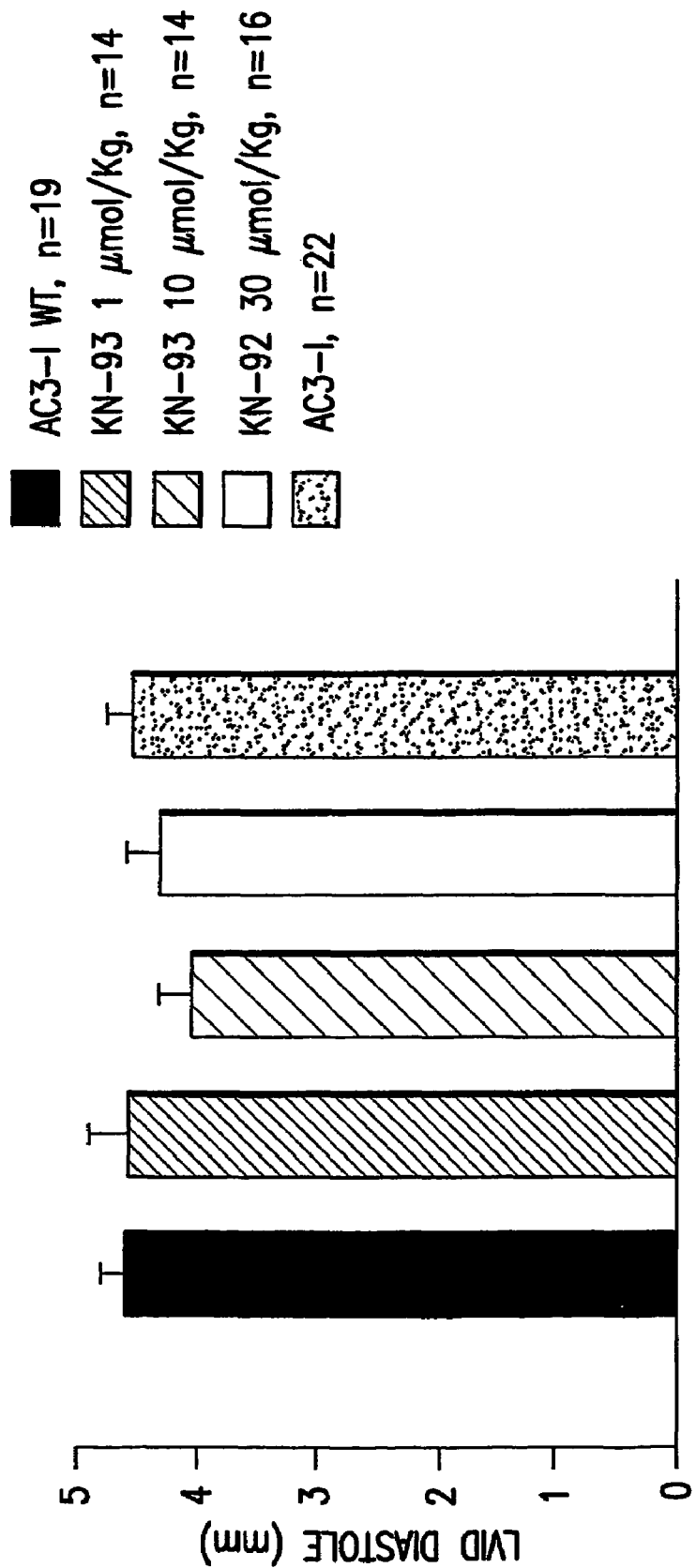
Figure 7C:
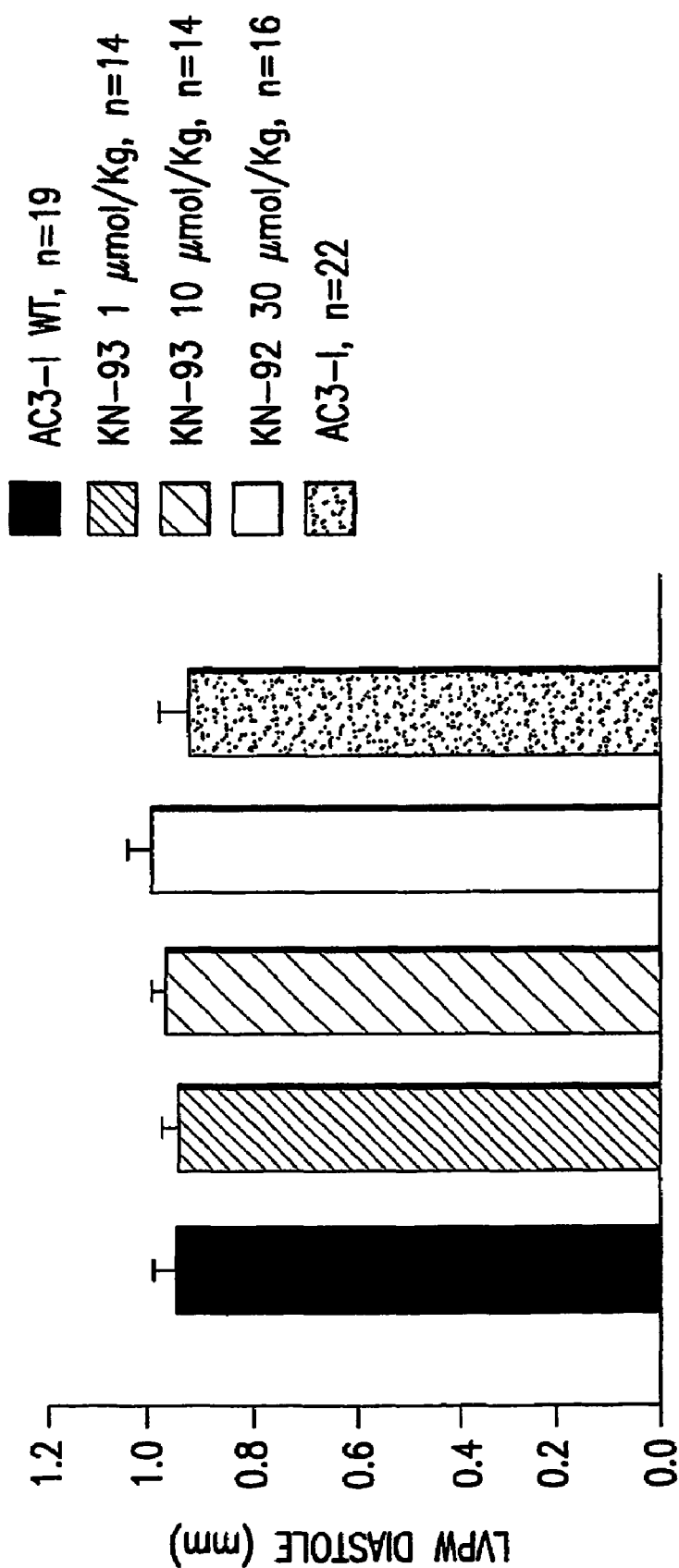
Figure 7D:
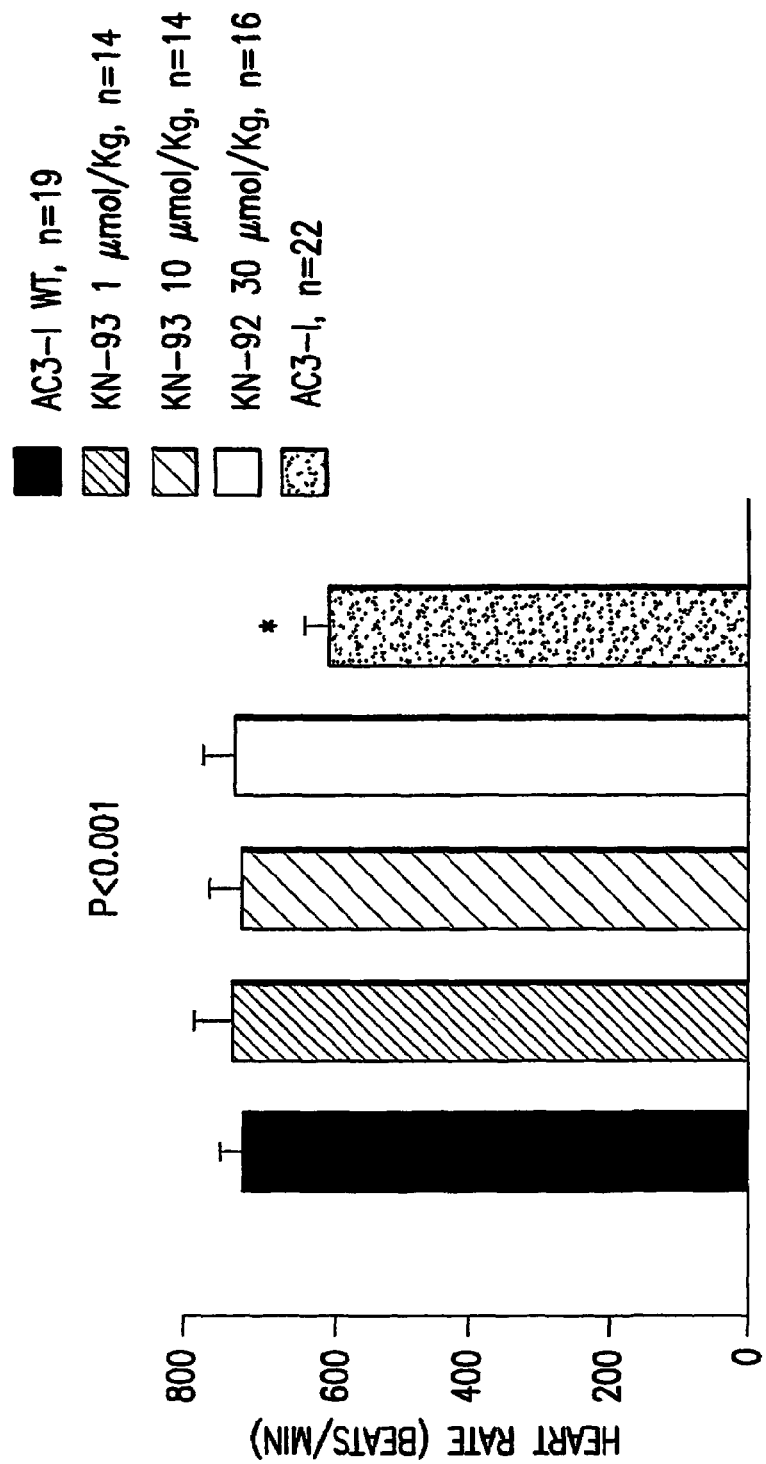
Figure 8A:
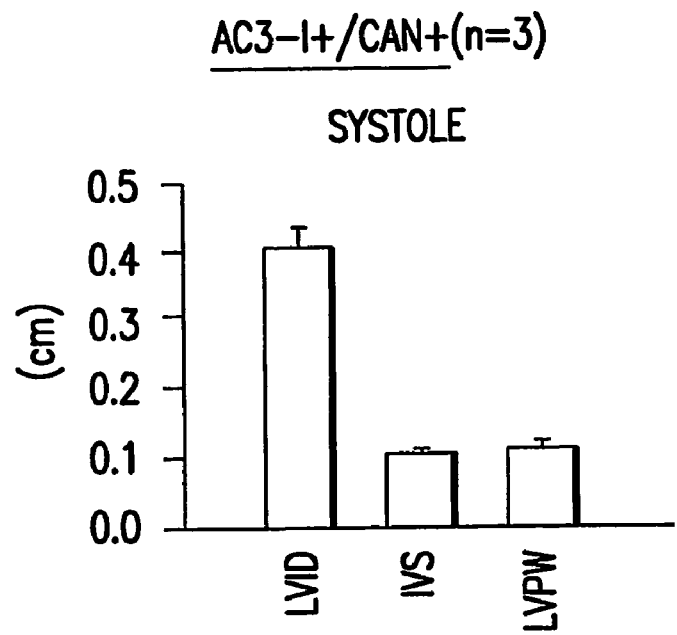
FIGS. 8A-C. CaMKII inhibition reduces left ventricular dilation and improves left ventricular contractile function in dilated cardiomyopathy. Dual transgenic (AC3-I+/CAN+) have reduced left ventricular (LV) dilation and improved LV fractional shortening compared to CAN+ transgenic mice.[10] Echocardiographic measurements in unanesthetized calcineurin (CAN+) transgenic and interbred dual transgenic AC3-I+/CAN+ mice show LV internal diameter (LVID) is significantly reduced in diastole and the interventricular septum (IVS) and the LV posterior wall (LVPW) are increased in diastole in AC3-I+/CAN+ compared to CAN+ mice, indicating partial rescue of the dilated cardiomyopathy phenotype by transgenically targeted CaMKII inhibition. Measurement parameters are the same for the top 4 panels: left ventricular internal diameter (LVID), interventricular septum (IVS), and left ventricular posterior wall (LVPW). Left ventricular systolic function is significantly increased in the dual transgenic AC3-I+/CAN+ mice compared to the CAN+ mice, indicating improved contractile function by transgenically targeted cardiac CaMKII inhibition. In contrast, there are no significant differences between heart rates in the AC3-I+/CAN+ and CAN+ transgenic animals. All mice were between 4-8 weeks of age.
Figure 8A:
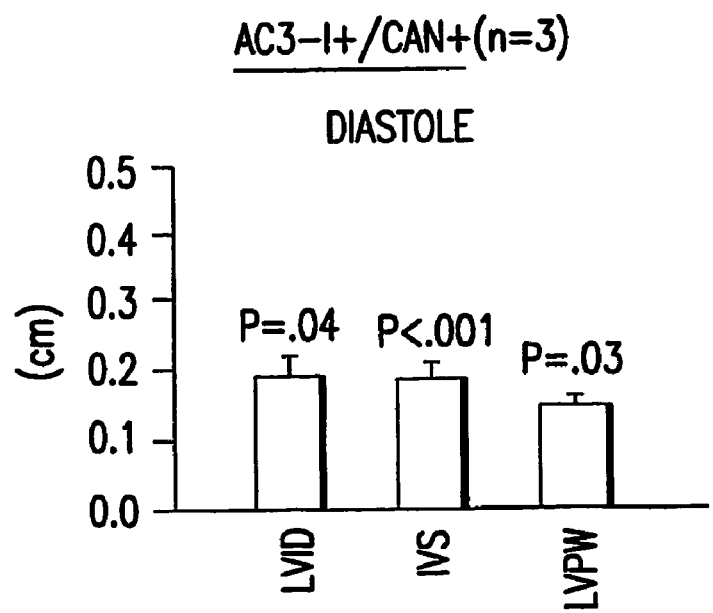
Figure 8B:
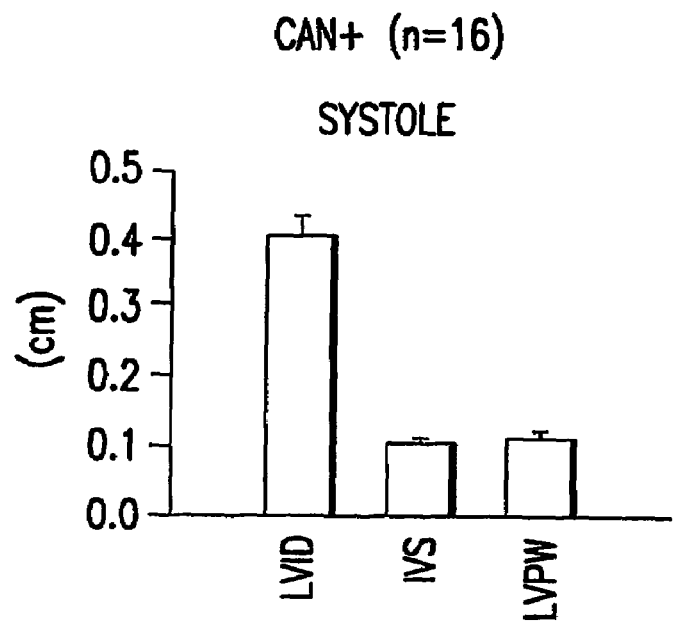
Figure 8B:
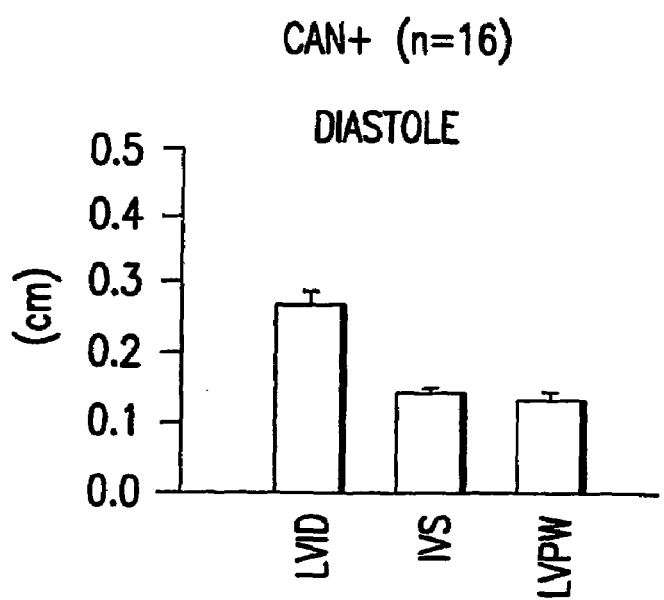
Figure 8C:
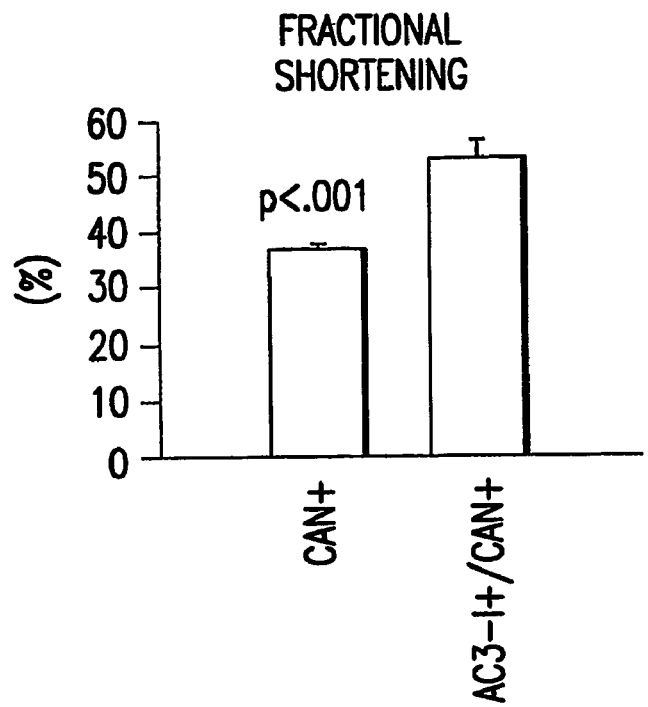
Figure 8C:
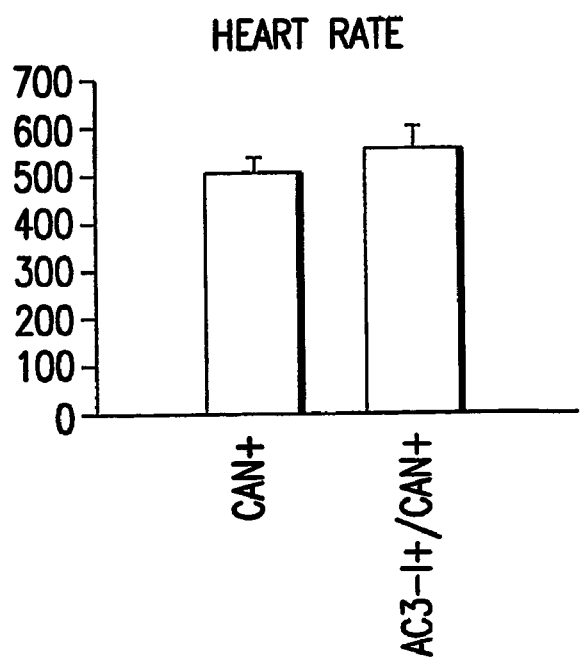

The invention further provides a transgenic animal which expresses in heart muscle cells a nucleic acid encoding a peptide comprising the peptide of SEQ ID NO:8, which is also referred to as AC3-C. As shown in FIGS. 4 and 5, AC3-I and AC3-C mice have similar expression of transgene, but AC3-C mice exhibit cardiomyopathy, whereas AC3-I mice with CaMKII inhibition are normal. As shown in FIG. 6, the AC3-C mice have high total CaMKII activity as is seen in human patients with cardiomyopathy. Thus, this transgenic animal can be used in the present method of identifying a compound that can treat structural heart disease. Because AC3-C is believed to be inactive, these results may be explained by an effect of the green fluorescent protein (GFP) moiety of the AC3-C-GFP transgene.[6] This mouse is made following the basic protocol for making the AC3-I transgenic mouse.

The present invention also provides a dual transgenic animal (AC3-I+/CAN+) which expresses in heart muscle cells a nucleic acid encoding AC3-I and a nucleic acid encoding calcineurin. The calcineurin (CAN+) transgenic mouse is a well accepted model of severe dilated cardiomyopathy.[10] CAN antagonists are known to 'rescue' the cardiomyopathy phenotype in a variety of mouse models,[16] but CaMKII inhibition has never been contemplated to improve cardiac function or structure in these or any other models of cardiomyopathy. As exemplified in FIG. 8, the dual transgenic animal, which expresses an inhibitor of CaMKII in addition to CAN, improves left ventricular function and shows reduced left ventricular dilation and hypertrophy when compared to CAN+ animals. Thus, inhibition of CaMKII in this animal treats dilated cardiomyopathy.

In the methods of the invention, an inhibitor of CaMKII can be administered by known means. In a specific example, the peptide inhibitors are made cell membrane permeant. By cell "membrane permeant" is meant able to pass through the openings or interstices in a membrane[16]. This method uses a peptide sequence that is added to the inhibitory peptide, but myristoylation is another approach for making a peptide cell membrane permeant.

The compositions of the present invention can also be administered in vivo in a pharmaceutically acceptable carrier. By "pharmaceutically acceptable" is meant a material that is not biologically or otherwise undesirable, i.e., the material may be administered to a subject, along with the composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously, intramuscularly, intrathecally, intraarterially and by intraperitoneal injection), transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the therapeutic agent. Delivery can also be directly to any part of the lower respiratory tract (e.g., trachea, bronchi and lungs) via intubation. The exact amount of the compositions required will vary from subject to subject, depending on the species, age, weight and general condition of the subject, the severity of the condition being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. The molecular and cellular mechanisms of receptor-mediated endocytosis have been reviewed (Brown and Greene, *DNA and Cell Biology* 10:6, 399-409 (1991)).

The compositions of the present invention can include a nucleic acid encoding an inhibitor or can include a CaMKII antisense nucleic acid. The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms.

As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of delivery, such as a liposome, so that the nucleic acid contained in the delivery system can be come integrated into the host genome. As used herein, "nucleic acid" includes single- or double-stranded molecules which may be DNA, comprised of the nucleotide bases A, T, C, G or RNA, comprised of the bases A, U (substitutes for T), C and G. The nucleic acid may represent a coding strand or its complement. Nucleic acids may be identical in sequence to the portion of the sequence which is naturally occurring or may include alternative codons which encode the same amino acid as that which is found in the naturally occurring sequence. Furthermore, nucleic acids can include codons which represent conservative substitutions of amino acids as are well known in the art.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. Those of skill in the art know these systems and the methods necessary to promote homologous recombination.

As described above, the compositions can be administered in a pharmaceutically acceptable carrier and can be delivered to the cells of the subject in vivo and/or ex vivo by a variety of mechanisms well known in the art (e.g., uptake of naked DNA, liposome fusion, intramuscular injection of DNA via a gene gun, endocytosis and the like). If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The inhibitor can be administered in any dose that is effective to inhibit CaMKII activity or amount. As noted above, detection of a reduction in CaMKII activity or amount is well within the skill of the practitioner. More specifically, the inhibitor can be administered in a dose of from about 0.05 mg to about 5.0 mg per kilogram of body weight. The inhibitor can, alternatively, be administered in a dose of from about 0.3 mg to about 3.0 mg per kilogram of body weight.

The following examples are put forth so as to provide those of ordinary skill in the art with a complete disclosure and description of how the compositions and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. The present invention is more particularly described in the following examples which are intended as illustrative only since numerous modifications and variations therein will be apparent to those skilled in the art.

EXAMPLES

AC3-I transgenic mice: The AC3-I mice were generated by synthesis of a minigene based on the peptide sequence for AC3-I (FIG. 1). A 'minigene' encoding AC3-I (KKALHRQEAVDCL),[2] a CaMKII inhibitory peptide was constructed with these complementary oligonucleotides:

GATCAAAAAAGCCCTTCACCGCCAGGAGGCAGTTGAC (SEQ ID NO:1)

TGCCTTGCTTTTTTCGGGAAGTGGCGGTCCTCCGTCA

ACTGACGGAACGCTAG, and a minigene was similarly constructed for a related, inactive control peptide, AC3-C (KKALHAQERVDCL) using the following complementary oligonucleotides:

GATCAAAAAAGCCCTTCACGCACAGGAGCGCGTTGAC (SEQ ID NO:7)

TGCCTTGCTTTTTTCGGGAAGTGCGTGTCCTCGCGCA

ACTGACGGAACGCTAG

The minigene was inserted in frame with the EGFP into the BspEI site of pEGFP-C1 (Clontech), which places the EGFP at the N-terminus of the peptide. The AC3-I minigene includes a Kozak consensus translational start site. It was then sequenced and expressed in HEK293 cells to show green fluorescence. Previous studies indicated that an AC3-I-GST-MTS fusion peptide retained full CaMKII inhibitory potency against a synthetic CaMKII substrate (AC3-I-GST-MTS $IC_{50}$=0.4 µM; AC3-I $IC_{50}$ 0.5 µM), suggesting that the AC3-I-GFP protein would also retain CaMKII inhibitory activity. The 800 bp AC3-I-GFP sequence was then amplified using PCR, purified and subcloned into the SalI site of a pBluescript vector containing the α-MHC promoter vector (GenBank accession U71441) and the human growth hormone (HGH) poly A tail (developed by Dr. J. Robbins). The construct was verified by sequencing and expressed in a murine atrial tumor cell line (HL1), which also showed green fluorescence. Murine embryonic stem cells were injected with the linearized DNA (2 ng/ml) in the Vanderbilt Transgenic Mouse core facility and implanted in B6D2 pseudo-pregnant females.

Figure 3A:
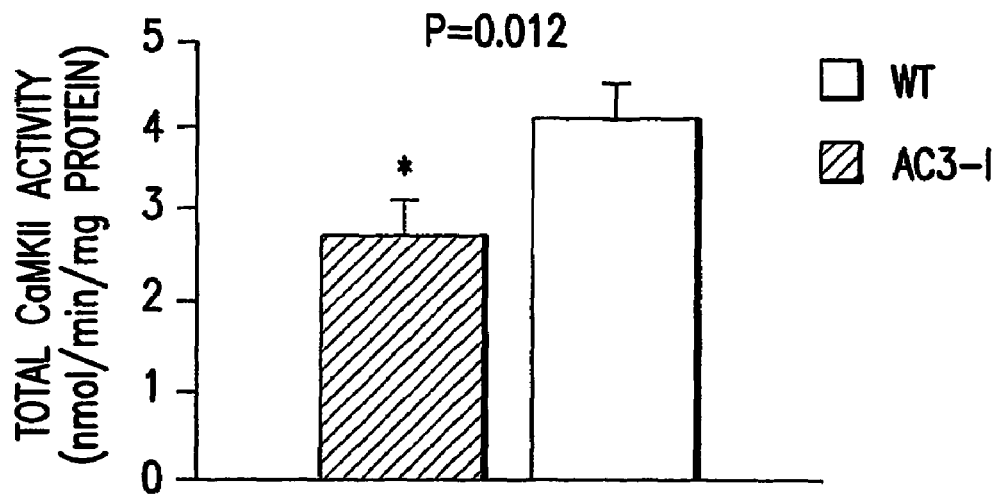
FIGS. 3A-B. AC3-I mice have significantly reduced cardiac CaMKII activity (A) and significantly better left ventricular fractional shortening after myocardial infarction surgery (B) than wild type (WT) littermate controls. CaMKII activity measurements are from whole heart homogenates.
Figure 3B:
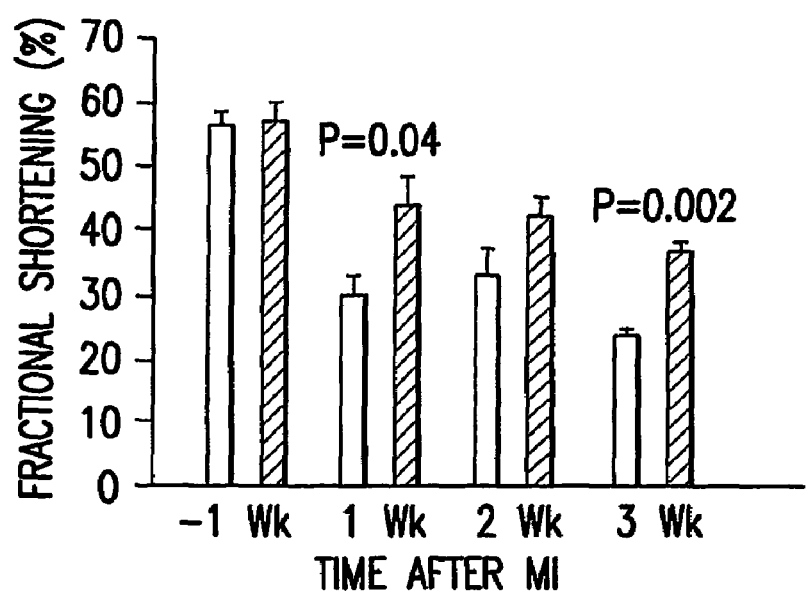

The AC3-I is linked to green fluorescent protein (GFP) to reveal homogenous expression throughout the heart when histologic sections are examined under a microscope. These AC3-I mice are viable and have normal basal cardiac size and function (FIG. 2). However, hearts from these mice have significantly reduced total cardiac CaMKII activity (FIG. 3(A)), and these mice have significantly less impairment of cardiac function after experimental myocardial infarction compared to wild type littermate controls (FIG. 3(B)). These findings indicate that CaMKII activity is a novel signal for cardiac dysfunction after myocardial infarction and are the basis for our claim to treat patients with myocardial infarction by a method of CaMKII inhibition.

AC3-I+/CAN+ transgeneic mice: Dual transgenic mice were interbred using the strategy schematized in FIG. 9. For genotyping of the first generation, tail biopsies were taken at 3 weeks of age and were incubated overnight at 55° C. in 0.5 Mg/ml protease K, 50 mM Tris (pH 8.0), 100 mM EDTA, and 0.5% SDS. Genomic DNA was precipitated with an equal volume of isopropanol after performing phenol/chloroform/isoamyl alcohol (25:24:1) extraction twice. DNA was dissolved overnight in 50 µl of ¹/₁₀ TE (pH 8.0) with 2.5 µg RNAase A. 15 µg of genomic DNA was completely digested with EcoRI and digested DNA was separated on a 0.8% agarose gel in 1×TAE. After electrophoresis, the gel was incubated in 0.25N HCL for 30 min, neutralized in 0.5M NaOH-1.5M NaCl for 15 min twice and equilibrated in 0.5M Tris-1.5M NaCl for 15 min twice. The gel was blotted overnight on MSI nylon transfer membrane (Micron separations Inc. Westborought, Mass.) and the filter was UV-crosslinked. GFP-AC3I or GFP-AC3C DNA fragments were labeled with $^{32}P$ by random oligonucleotide priming (Stratagene, La Jolla, Calif.) as a probe. Hybridization was carried out overnight at 42° C. in the presence of 50% Formamide, 5×SSPE, 5× Denhardt's solution, 0.1% SDS, and 1001 g/ml denatured, fragmented salmon sperm DNA. The filter was washed in 0.5×SSC-0.1% SDS for 30 min at 65° C., followed by a wash in 0.1×SSC-0.1% SDS for 20 min twice at 65° C. The filter was exposed to Kodak autoradiography film and developed afterwards.

Figure 9A:
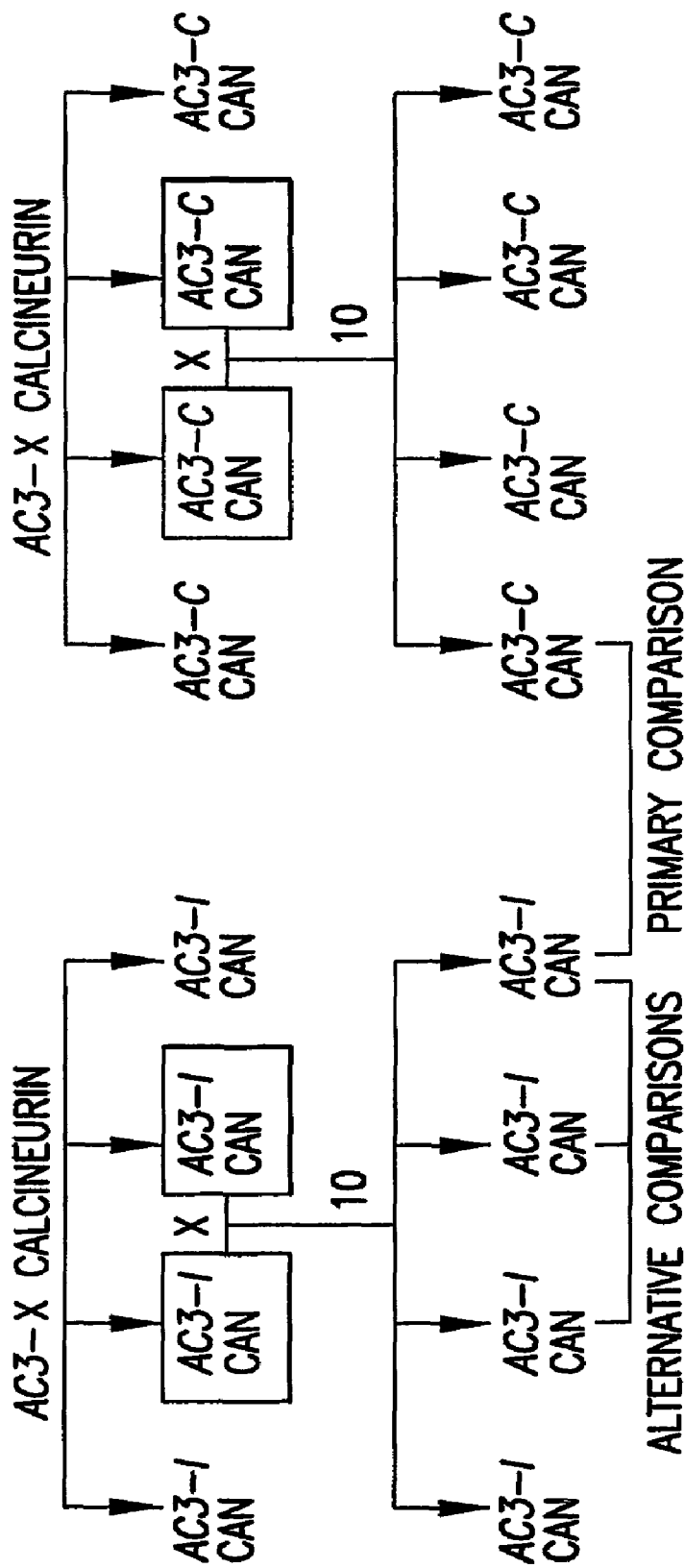
FIGS. 9A-B. Strategy for interbreeding AC3-I or AC3-C and Calcineurin (CAN) transgenic mice. A. Boxes indicate breeding pairs. The primary comparison will be between CAN positive mice, but alternative comparisons (that provide data shown in FIG. 8) are also shown. B. PCR results reveal that interbreeding between AC3-I and CAN mice is successful and that dual transgenic mice can be identified with standard PCR methods.
Figure 9B:
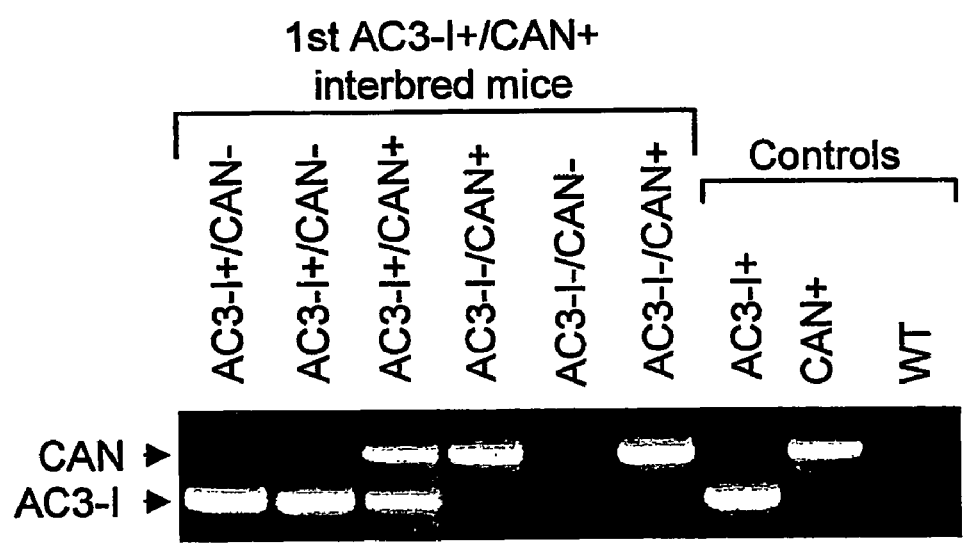

Routine screening of transgenic mice, after the first generation, was done by PCR (see FIG. 9). Two primers served to amplify a 442-bp region of the human growth hormone (hGH) gene at 3' end. The sequences of the primers are 5'-Hgh (5'-(SEQ ID NO:9) GTCTATTCGGGAAC-CAAGCT-3') and 3'-Hgh (5'-(SEQ ID NO:10) ACAG-GCATCTACTGAGTGGACC-3'). 100 ng purified genomic DNA was mixed with 200 pM of each primer and amplified according to the following protocol: 95° C. for 5 min, followed by 30 cycles consisting of 95° C. for 45 seconds, 50° C. for 45 seconds, 72° C. for 1 min and a final 7 min elongation at 72° C. All samples were run on a 1.5% agarose gel in the presence of 0.5 µg/ml ethidium bromide and stained DNA bands were visualized under UV light. New primer sets were developed for the interbred dual transgenic mice (FIG. 9) and these allow differentiation of dual and single transgenic animals.

Echocardiography: Echocardiography is performed using a Hewlett Packard Sonos 5500 (fully dedicated to murine studies) and a specially developed 12 MHz probe. Cardiac dimensions are obtained from 2-D-guided M mode images and are read off line by blinded, independent readers using short axis and a parasternal long-axis views with the leading edge method. Animals can be lightly sedated with pentobarbital (15 mg/Kg, i.p.); however, measurements without anesthesia, where the mice undergo a brief 'training' period to acclimate to the procedure, can be made. Approximately 90% of mice can be trained to undergo echocardiographic studies without the cardiodepressant effects of anesthesia. Measurements are averaged over 3 consecutive beats from the LV posterior wall (LVPW), the interventricular septum (IVS), and the LV internal diameter (LVID). Fractional shortening (FS) is used to estimate systolic function and is computed according to the formula FS=(LVIDdiastole-LVIDsystole)/LVIDdiastole×100.

Myocardial infarction surgery: Surgery is routinely performed at the Vanderbilt mouse physiology core laboratory and is essentially identical to other published reports [18,8,14]. In brief, mice are anesthetized (pentobarbital 33 μg/g and ketamine 33 μg/g, i.p.) and placed on a rodent respirator (tidal vol. 0.5 ml, rate 120 breaths/min), the chest opened with a left parasternal thoracotomy, and the region of the mid-left anterior descending artery ligated with 8-0 suture. The chest is closed (running 5-0 suture), and the animal weaned from the respirator. Wild-type mice typically develop heart failure, as assessed by increased lung wet:dry weights. Sham operations omit the ligation step. Approximately 75% of animals survive surgery with a successfully infarcted anterior wall.

CaMKII activity assays: CaMKII activity was assayed in AC3-I mice and littermate controls from whole heart (ventricular) homogenate with syntide 2-a synthetic substrate with ~50 fold selectivity for CaMKII over CaMKIV,[9] using our previously published methods.[1]

Dilated cardiomyopathy: Compelling data are presented on prevention of dilated cardiomyopathy by CaMKII inhibition. A control transgenic mouse that expresses GFP linked to AC3-C (an inactive congener of AC3-I) was made. This mouse develops rather severe dilated cardiomyopathy that is absent in the AC3-I-GFP mouse, and has very high levels of CaMKII activity (FIG. 5).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Anderson M., Braun A., Wu Y., Lu T., Schulman H., Sung R. KN-93, an inhibitor of multifunctional Ca++/calmodulin-dependent protein kinase, decreases early afterdepolarizations in rabbit heart. J Pharm Exp Ther 1998;287:996-1006.
2. Braun A., Schulman H. A non-selective cation current activated via the multifunctional Ca(2+)-calmodulin-dependent protein kinase in human epithelial cells. J Physiol 1995;488:37-55.
3. Braun A., Schulman H. The multifunctional calcium/calmodulin-dependent protein kinase: from form to function. Ann Rev Physiol 1995;57:417-445.
4. Gottlieb S., McCarter R., Vogel R. Effect of beta-blockade on mortality among high-risk and low-risk patients after myocardial infarction. [see comments]. New England Journal of Medicine 1998;339:489-497.
5. Hoch B., Meyer R., Hetzer R., Krause E., Karczewski P. Identification and expression of delta-isoforms of the multifunctional Ca2+/calmodulin-dependent protein kinase in failing and nonfailing human myocardium. Circulation Research 1999;84:713-721.
6. Huang W., Aramburu J., Douglas P., Izumo S. Transgenic expression of green fluorescence protein can cause dilated cardiomyopathy. Nat Med 2000;6:482-483.
7. Hunt S., Baker D., Chin M., Cinquegrani M., Feldman A., Francis G., Ganiats T., Goldstein S., Gregoratos G., Jessup M., Noble R., Paclcer M., Silver M., Stevenson L., Gibbons R., Antman E., Alpert J., Faxon D., Fuster V., Jacobs A., Hiratzka L., Russell R., Smith S., Jr., American College of Cardiology/American Heart Association. ACC/AHA guidelines for the evaluation and management of chronic heart failure in the adult: executive summary. A report of the American College of Cardiology/American Heart Association Task Force on Practice Guidelines (Committee to revise the 1995 Guidelines for the Evaluation and Management of Heart Failure). Journal of the American College of Cardiology 2001;38:2101-2113.
8. Kinugawa S., Tsutsui H., Hayashidani S., Ide T., Suematsu N., Satoh S., Utsumi H., Takeshita A. Treatment with dimethylthiourea prevents left ventricular remodeling and failure after experimental myocardial infarction in mice: role of oxidative stress. Circulation Research 2000;87:392-398.
9. Miyano O., Kameshita I., Fujisawa H. Purification and characterization of a brain-specific multifunctional calmodulin-dependent protein kinase from rat cerebellum. J Biol Chem 1992;267:1198-1203.
10. Molkentin J., Lu J., Antos C., Markham B., Richardson J., Robbins J., Grant S., Olson E. A calcineurin-dependent transcriptional pathway for cardiac hypertrophy. Cell 1998;93:215-228.
11. Pfeffer J., Fischer T., Pfeffer M. Angiotensin-converting enzyme inhibition and ventricular remodeling after myocardial infarction. Ann Rev Physiol 1995;57:805-826.
12. Pitt B., Zannad F., Remme W., Cody R., Castaigne A., Perez A., Palensky J., Wittes J. The effect of spironolactone on morbidity and mortality in patients with severe heart failure. Randomized Aldactone Evaluation Study Investigators. New England Journal of Medicine 1999;341:709-717.
13. Rhoads A., Friedberg F. Sequence motifs for calmodulin recognition. FASEB 1997;11:331-340.
14. Sam F., Sawyer D., Chang D., Eberli F., Ngoy S., Jain M., Amin J., Apstein C., Colucci W. Progressive left ventricular remodeling and apoptosis late after myocardial infarction in mouse heart. American Journal of Physiology—Heart & Circulatory Physiology 2000;279:H422-H428.
15. Spencer F., Meyer T., Goldberg R., Yarzebski J., Hatton M., Lessard D., Gore J. Twenty year trends (1975-1995) in the incidence, in-hospital and long-term death rates associated with heart failure complicating acute myocardial infarction: a community-wide perspective. J Am Coll Cardiol 1999;34:1378-1387.
16. Sussman M., Lim H., Gude N., Taigen T., Olson E., Robbins J., Colbert, M C, Gualberto A., Wieczorek D., Molkentin J. Prevention of cardiac hypertrophy in mice by calcineurin inhibition [see comments]. Science 1998;281:1690-1693.
17. Tokumitsu H., Brickey D., Glod J., Hidaka H., Silcela J., Soderling T. Activation mechanisms for Ca2+/calmodulin-dependent protein kinase IV. Identification of a brain CaM-kinase IV kinase. J Biol Chem 1994;269:28640-28647.

18. Trueblood N., Xie Z., Communal C., Sam F., Ngoy S., Liaw L., Jenkins A., Wang J., Sawyer D., Bing O., Apstein C., Colucci W., Singh K. Exaggerated left ventricular dilation and reduced collagen deposition after myocardial infarction in mice lacking osteopontin. Circulation Research 2001;88:1080-1087.

19. Vaughan D., Pfeffer M. Post-myocardial infarction ventricular remodeling: animal and human studies. Cardiovascular Drugs & Therapy 1994;8:453-460.

20. Wu Y., MacMillan L., McNeill R., Colbran R., Anderson M. CaM kinase augments cardiac L-type Ca2+ current: a cellular mechanism for long Q-T arrhythmias. American Journal of Physiology 1999;276:H2168-H2178.

21. Wu Y. Calmodulin kinase II and arrhythmias in a mouse model of cardiac hypertrophy. Circ 2002;106:1288-1293.

What is claimed is:

1. A method of treating myocardial contractile dysfunction after myocardial infarction in a subject, comprising administering to the subject an effective amount of an inhibitor of Calmodulin Kinase II (CaMKII), whereby the administration of the inhibitor treats post-myocardial infarction myocardial contractile dysfunction in the subject.

2. The method of claim 1, wherein the inhibitor of CaMKII is a peptide comprising the peptide of SEQ ID NO:2.

3. The method of claim 2, wherein the inhibitor is the peptide of ID. NO:2.

4. The method of claim 1, wherein the inhibitor is KN-93.

5. The method of claim 1, wherein the inhibitor is administered in a dose of from about 0.05 mg to about 5.0 mg per kilogram of body weight.

6. The method of claim 1, wherein the inhibitor is administered in a dose of from about 0.3 mg to about 3.0 mg per kilogram of body weight.

7. A method of treating dilated cardiomyopathy in a subject diagnosed with dilated cardiomyopathy, comprising administering to the subject an effective amount of an inhibitor of Calmodulin Kinase II (CaMKII), whereby the administration of the inhibitor treats dilated cardiomyopathy in the subject.

8. The method of claim 7, wherein the inhibitor of CaMKII is a peptide comprising the peptide of SEQ ID NO:2.

9. The method of claim 8, wherein the inhibitor is the peptide of SEQ ID NO:2.

10. The method of claim 7, wherein the inhibitor is KN-93.

11. The method of claim 7, wherein the inhibitor is administered in a dose of from about 0.05 mg to about 5.0 mg per kilogram of body weight.

12. The method of claim 7, wherein the inhibitor is administered in a dose of from about 0.3 mg to about 3.0 mg per kilogram of body weight.

13. A method of increasing myocardial contractility in a subject diagnosed with dilated cardiomyopathy, comprising administering to the subject an effective amount of an inhibitor of CaMKII, whereby the administration of the inhibitor increases myocardial contractility in the subject.

14. The method of claim 13, wherein the inhibitor of CaMKII is a peptide comprising the peptide of SEQ ID NO:2.

15. The method of claim 14, wherein the inhibitor is the peptide of SEQ ID NO:2.

16. The method of claim 13, wherein the inhibitor is administered in a dose of from about 0.05 mg to about 5.0 mg per kilogram of body weight.

17. The method of claim 13, wherein the inhibitor is administered in a dose of from about 0.3 mg to about 3.0 mg per kilogram of body weight.

18. A method of increasing myocardial contractility in a subject diagnosed with decreased myocardial contractility, comprising administering to the subject an effective amount of an inhibitor of CaMKII, whereby the administration of the inhibitor increases myocardial contractility in the subject.

19. The method of claim 18, wherein the of CaMKII is a peptide comprising the peptide of SEQ ID NO:2.

20. The method of claim 19, wherein the inhibitor is the peptide of SEQ ID NO:2.

21. The method of claim 18, wherein the inhibitor is KN-93.

22. The method of claim 18, wherein the inhibitor is administered in a dose of from about 0.05 mg to about 5.0 mg per kilogram of body weight.

23. The method of claim 18, wherein the inhibitor is administered in a dose of from about 0.3 mg to about 3.0 mg per kilogram of body weight.

24. A method of increasing myocardial contractility in a subject diagnosed with cardiac structural dysfunction following a myocardial infarction, comprising administering to the subject an effective amount of an inhibitor of CaMKII, whereby the administration of the inhibitor increases myocardial contractility in the subject.

25. The method of claim 24, wherein the inhibitor of CaMKII is a peptide comprising the peptide of SEQ ID NO:2.

26. The method of claim 25, wherein the inhibitor is the peptide of SEQ ID NO:2.

27. The method of claim 24, wherein the inhibitor is KN-93.

28. The method of claim 24, wherein the inhibitor is administered in a dose of from about 0.05 mg to about 5.0 mg per kilogram of body weight.

29. The method of claim 24, wherein the inhibitor is administered in a dose of from about 0.3 mg to about 3.0 mg per kilogram of body weight.

* * * * *

SEQUENCE LISTING

<160> NUMBER OF SEQ ID NOS: 10

<210> SEQ ID NO 1
<211> LENGTH: 90
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 1

```
gatcaaaaaa gcccttcacc gccaggaggc agttgactgc cttgcttttt tcgggaagtg      60
gcggtcctcc gtcaactgac ggaacgctag                                      90
```

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 2

Lys Lys Ala Leu His Arg Gln Glu Ala Val Asp Cys Leu
 1               5                  10

<210> SEQ ID NO 3
<211> LENGTH: 255
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 3

```
cggctcccct gctgagctag ggccggtccg gcagtcagcc tctgcccgtg ccccgccgca      60
gtccctagcc cgcccggtgc ccgccgcctg caggacacca actccttctt cgctggcaac     120
caggccaagc ggcccccccaa gctgggccag atcggccgag ccaagagagt ggtgatcgag    180
gatgaccgga tagacgacgt gctgaagggg atgggggaga agcctccgtc cggagtgtag    240
acgcgccggc tctgg                                                      255
```

<210> SEQ ID NO 4
<211> LENGTH: 79
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 4

Met Ser Glu Ile Leu Pro Tyr Gly Glu Asp Lys Met Gly Arg Phe Gly
 1               5                  10                  15

Ala Asp Pro Glu Gly Ser Asp Leu Ser Phe Ser Cys Arg Leu Gln Asp
            20                  25                  30

Thr Asn Ser Phe Phe Ala Gly Asn Gln Ala Lys Arg Pro Pro Lys Leu
        35                  40                  45

Gly Gln Ile Gly Arg Ala Lys Arg Val Val Ile Glu Asp Asp Arg Ile
    50                  55                  60

Asp Asp Val Leu Lys Gly Met Gly Glu Lys Pro Pro Ser Gly Val
65                  70                  75

<210> SEQ ID NO 5
<211> LENGTH: 129
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 5
aagcggcccc ccaagctggg ccagatcggc cgagccaaga gagtggtgat cgaggatgac      60
cggatagacg acgtgctgaa ggggatgggg gagaagcctc cgtccggagt gtagacgcgc    120
cggctctgg                                                            129

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 6

Lys Arg Pro Pro Lys Leu Gly Gln Ile Gly Arg Ala Lys Arg Val Val
1               5                   10                  15

Ile Glu Asp Asp Arg Ile Asp Asp Val Leu Lys
            20                  25

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 7
gatcaaaaaa gcccttcacg cacaggagcg cgttgactgc cttgcttttt tcgggaagtg     60
cgtgtcctcg cgcaactgac ggaacgctag                                     90

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 8

Lys Lys Ala Leu His Ala Gln Glu Arg Val Asp Cys Leu
1               5                   10

<210> SEQ ID NO 9
<211> LENGTH: 20

-continued

```
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 9
gtctattcgg gaaccaagct                                              20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 10
acaggcatct actgagtgga cc                                           22
```